US010799135B2

(12) United States Patent
Bornzin et al.

(10) Patent No.: US 10,799,135 B2
(45) Date of Patent: Oct. 13, 2020

(54) METHOD AND SYSTEM TO DETECT R-WAVES IN CARDIAC ACTIVITY SIGNALS

(71) Applicant: PACESETTER, INC., Sytlmar Sylmar, CA (US)

(72) Inventors: Gene A. Bornzin, Simi Valley, CA (US); Fady Dawoud, Santa Monica, CA (US); Jong Gill, Valencia, CA (US); Stuart Rosenberg, Castaic, CA (US); Fujian Qu, San Jose, CA (US); Neha Malhotra, Los Angeles, CA (US)

(73) Assignee: PACESETTER, INC., Sylmar, CA (US)

( * ) Notice: Subject to any disclaimer, the term of this patent is extended or adjusted under 35 U.S.C. 154(b) by 198 days.

(21) Appl. No.: 16/007,878

(22) Filed: Jun. 13, 2018

(65) Prior Publication Data
US 2019/0380610 A1    Dec. 19, 2019

(51) Int. Cl.
| | |
|---|---|
| *A61N 1/04* | (2006.01) |
| *A61B 5/04* | (2006.01) |
| *A61B 5/0468* | (2006.01) |
| *A61B 5/0432* | (2006.01) |
| *A61B 5/042* | (2006.01) |
| *A61B 5/0456* | (2006.01) |
| *A61B 5/00* | (2006.01) |

(52) U.S. Cl.
CPC .......... *A61B 5/04017* (2013.01); *A61B 5/042* (2013.01); *A61B 5/0432* (2013.01); *A61B 5/0456* (2013.01); *A61B 5/0468* (2013.01); *A61B 5/7203* (2013.01)

(58) Field of Classification Search
None
See application file for complete search history.

(56) References Cited

U.S. PATENT DOCUMENTS

| | | | |
|---|---|---|---|
| 5,065,766 A | 11/1991 | Sasaki | |
| 5,999,850 A | 12/1999 | Dawson et al. | |
| 7,027,858 B2 | 4/2006 | Cao et al. | |
| 8,849,388 B2 | 9/2014 | Brodnick et al. | |
| 2006/0235476 A1* | 10/2006 | Gunderson | A61B 5/0456 607/5 |
| 2017/0273589 A1* | 9/2017 | Sarkar | A61B 5/6861 |
| 2017/0368360 A1* | 12/2017 | Hahn | A61N 1/36514 |
| 2018/0028828 A1* | 2/2018 | Cao | A61B 5/04011 |

* cited by examiner

*Primary Examiner* — Ankit D Tejani
(74) *Attorney, Agent, or Firm* — Dean D. Small; The Small Patent Law Group, LLC

(57) ABSTRACT

A computer Implemented method and system for detecting arrhythmias in cardiac activity are provided. The method is under control of one or more processors configured with specific executable instructions. The method obtains far field cardiac activity (CA) signals and applies a direction related responsiveness (DRR) filter to the CA signals to produce DRR filtered signals. The method compares a current sample from the CA signals to a prior sample from the DRR filtered signals to identify a direction characteristic of the CA signals and defines the DRR filter based on a timing constant that is set based on the direction characteristic identified. The method analyzes the CA signals in connection with the DRR filtered signals to identify a peak characteristic of the CA signals and determines peak to peak intervals between successive peak characteristic. The method detects at least one of noise or an arrhythmia based on the peak to peak intervals and records results of the detecting.

20 Claims, 17 Drawing Sheets

METHOD AND SYSTEM TO DETECT R-WAVES IN CARDIAC ACTIVITY SIGNALS

FIELD OF THE INVENTION

Embodiments herein relate generally to implantable medical devices, and more particularly to detection of R-waves and discrimination of noise in cardiac activity signals.

BACKGROUND OF THE INVENTION

Atrial fibrillation (AF) is a common and serious cardiac arrhythmia, affecting more than two million people in the United States alone. Clinically, atrial fibrillation involves an abnormality of electrical impulse formation and conduction that originates in the atria. Atrial fibrillation is characterized by multiple swirling wavelets of electrical current spreading across the atria in a disorganized manner. The irregularity of electrical conduction throughout the atria creates irregular impulse propagation through the atrioventricular (AV) node into the ventricle.

Impulse propagation through the AV node may be extremely rapid, leading to reduced diastolic filling of the heart chambers and a corresponding reduction of the cardiac pumping action. Increased heart rate and loss of AV synchrony may also exacerbate any underlying heart problems, such as heart failure, coronary blood flow, or other pulmonary disorders. Alternatively, impulse propagation through the AV node may be very limited due to AV node refractoriness so that atrial fibrillation can be sustained indefinitely, as the ventricles continue to drive circulation, albeit inefficiently.

Atrial Fibrillation (AF) monitoring systems have been developed for use in an ambulatory setting, which may be either external, such as a Holter monitor, or internal, such as implantable cardiac monitors or "loop recorders". These systems continually sense cardiac electrical signals from a patient's heart, process the signals to detect arrhythmias and upon detection, record the electrical signals for subsequent review and analysis.

More recently, interest has increased in providing improved implantable cardiac monitors. It has been proposed that implantable cardiac monitors may be used for diagnosis of re-current AF after AF ablation, cryptogenic stroke, and other arrhythmias. Further, there is an interest in improved management of arrhythmia episodes in connection with medication usage, as well as monitoring AF in connection with periodic atrial cardioversion.

Algorithms used by existing implantable cardiac monitoring devices for detecting AF are primarily based on an irregularity of R-R intervals. However, these algorithms may provide false positive AF detections when AF did not necessarily exist. As one example, certain AF detection algorithms may be confused when a patient exhibits sinus rhythm with irregular R-R intervals and/or when R-waves are under-sensed by the implantable cardiac monitoring device. R-wave under-sensing is attributable, in part, to variability of R-waves inherently associated with the subcutaneous implant of an implantable cardiac monitoring device. Changes in posture, body-motion and position tend to change the electrode location and cause sudden changes in the EGM amplitude. R-wave under-sensing results in missed R-waves that leads to a false indication of a bradycardic event.

Further, existing AF detection algorithms may experience undue false positives in connection with frequent premature ventricular contraction (PVC). Existing AF algorithms may not exhibit sufficient positive predictive value (PPV) of AF episode detection and duration (burden).

FIG. 1B illustrates a conventional sensitivity profile followed by an automatic sensing control (ASC) algorithm utilized by a conventional AF detection algorithm. FIG. 1B illustrates an example rectified cardiac activity (CA) signals 151 that is used by an implantable cardiac monitor (ICM) to manage a sensing circuit to have a sensitivity profile 153 (denoted by a dashed line) that varies over time. In a basic implementation, the sensitivity profile 153 is defined by programmed sensitivity profile parameter settings corresponding to the threshold start sensitivity 161, decay delay parameter 169, maximum sensitivity 157 and slope of the sensitivity decay 165. The start sensitivity parameter defines a start sensitivity of the sensitivity profile. The refractory period/interval duration parameter defines a blanking interval beginning at a sensed R-wave, during which the processors do not search for a T-wave. The decay delay parameter defines the interval at which the sensitivity profile maintains the sensitivity level at a constant level following expiration of the refractory period before the sensitivity profile begins decreasing. The maximum sensitivity limit defines a lowest sensitivity level (e.g., maximum resolution) that linear sensitivity decline is allowed to reach. The sensitivity parameters are preprogrammed to fixed values and, over the operation of the implantable medical device, are only modified (if at all) by a clinician.

In accordance with the sensitivity profile 153, when the CA signals 151 crosses the sensitivity profile 153 at starting point 155, the ICM treats the point 155 as a sensed R-wave and begins a refractory interval 159. No new R-wave (or T-wave) will be sensed during the refractory interval 159. At the end of the refractory interval 159, the sensitivity is adjusted to a threshold start sensitivity 161. The threshold start sensitivity 161 is defined as a percentage of the peak amplitude 163 of the QRS complex of the CA signal 151 detected during the refractory interval 159. The sensing circuit maintains the threshold start sensitivity 161 for a decay delay parameter 169, after which the ICM begins to monotonically decrease the sensitivity (increase the resolution) of the sensing circuit 144 as denoted by the sensitivity decay 165 within the sensitivity profile 153. The sensing circuit continues to decrease the sensitivity until either the sensitivity decay 165 reaches the maximum sensitivity 157 or an amplitude of the rectified cardiac activity signal 151 exceeds the sensor sensitivity profile 153, such as at a point 167 where a new sensed R wave is detected.

The parameters of the ASC algorithm are defined at the time of implant by a clinician and may be reprogrammed during a patient visit to a doctor's office. However, one difficulty with the conventional ASC algorithm is that a maximum sensitivity does not go below a programmed lowest sensitivity limit (e.g., 0.5 mV) which contributes to under-sensing of R-waves. Another difficulty is that the sensitivity level drops at the rate defined by the linear decay parameter which may cause the sensitivity level to drop below a level of a T-wave, thereby leading to T-wave over sensing (e.g., detecting T-waves as R-waves).

An opportunity remains to improve the accuracy of ICMs for sensing R-waves, discriminating noise, generating accurate diagnostics and computing short/long term trends in physiological signals leading to actionable insights and predictions. Although recent improvements have been made in implantable device hardware, filters, and sensing algorithms, false detection of bradycardia and asystole episodes remains a challenge due to small amplitude signals, premature ventricular contraction (PVC) beats, sudden drops in signal amplitude, suboptimal device programming, and loss of contact between subcutaneous tissue and electrodes. Improved sensing algorithm performance could lead to reduced unnecessary data transmission to remote clinicians, episode review burden, and potentially prolong ICM longevity.

SUMMARY

In accordance with embodiments herein, a computer implemented method for detecting arrhythmias in cardiac activity is provided. The method is under control of one or more processors configured with specific executable instructions. The method obtains far field cardiac activity (CA) signals and applies a direction related responsiveness (DRR) filter to the CA signals to produce DRR filtered signals. The method compares a current sample from the CA signals to a prior sample from the DRR filtered signals to identify a direction characteristic of the CA signals and defines the DRR filter based on a timing constant that is set based on the direction characteristic identified. The method analyzes the CA signals in connection with the DRR filtered signals to identify a peak characteristic of the CA signals and determines peak to peak intervals between successive peak characteristic. The method detects at least one of noise or an arrhythmia based on the peak to peak intervals and records results of the detecting.

Optionally, the method may set the time constant to a first value when the direction characteristic indicates an increasing trend in the CA signals and may set the time constant to a second value when the direction characteristic indicates a decreasing trend in the CA signals. The first value may represent a time constant that is shorter than the second value. The first value may be used by the DRR filter to produce the DRR filtered signals that respond to the decreasing trend in the CA signals more slowly as compared to a responsiveness of the DRR filter when set to the second value in response to the increasing trend in the CA signals. The analyzing operation may comprise determining a difference between the current sample of the CA signals and a prior sample of the DRR filtered signals and determines whether the difference exceeds a threshold.

Optionally, the method may further comprise declaring detection of a peak of an R-wave when the difference exceeds the threshold. The analyzing may comprise identifying the peak characteristic as a peak of an R-wave. The determining may comprise determining the peak to peak intervals as RR intervals. The detecting may comprise detecting the arrhythmia based on the RR intervals. The analyzing may comprise identifying the peak characteristic as a noise peak. The determining may comprise declaring a noise peak to peak (NPP) interval when the peak to peak interval is below a threshold.

Optionally, the method may comprise declaring a segment of the CA signals to include excessive noise when a select number of the peak to peak intervals are declared to be NPP intervals. The method may remove the segment of the CA signals to form noise corrected CA signals, and repeating the applying, comparing, defining, analyzing, determining and detecting operations utilizing a DRR filter and time constant set for R-wave detection.

In accordance with embodiments herein, a system for detecting arrhythmias in cardiac activity is provided. The system comprises memory to store specific executable instructions. One or more processors are configured to execute the specific executable instructions for obtaining far field cardiac activity (CA) signals for beats and applying a direction related responsiveness (DRR) filter to the CA signals to produce DRR filtered signals. The system compares a current sample from the CA signals to a prior sample from the DRR filtered signals to identify a direction characteristic of the CA signal and defines the DRR filter based on a timing constant that is set based on the direction characteristic identified. The system analyzes the CA signals in connection with the DRR filtered signals to identify a peak characteristic of the CA signals and determines peak to peak intervals between successive peak characteristics. They system detects at least one of noise or an arrhythmia based on the peak to peak intervals and records results of the detecting.

Optionally, the one or more processors may be further configured for setting the time constant to a first value when the direction characteristic indicates an increasing trend in the CA signals and setting the time constant to a second value when the direction characteristic indicates a decreasing trend in the CA signals. The first value may represent a time constant that is shorter than the second value. The one or more processors may be further configured for determining a difference between the current sample of the CA signals and a prior sample of the DRR filtered signals and determining whether the difference exceeds a threshold. The one or more processors may be further configured for declaring detection of a peak of an R-wave when the difference exceeds the threshold. The one or more processors may be further configured for identifying the peak characteristic as a peak of an R-wave.

Optionally, determining may comprise determining the peak to peak intervals as RR intervals. The detecting may comprise detecting the arrhythmia based on the RR intervals. The analyzing may comprise identifying the peak characteristic as a noise peak. The determining may comprise declaring a noise peak to peak (NPP) interval when the peak to peak interval is below a threshold. The system may further comprise an implantable medical device housing the processor and memory. The processor and memory may be housed within at least one of a local external device and a remote server. The one or more processors may be configured to perform the repeating the applying, comparing, defining, analyzing, determining and detecting operations in connection with at least one of i) an arrhythmia first pass detection process or ii) an arrhythmia second pass confirmation process.

DETAILED DESCRIPTION

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes.

The terms "beat" and "cardiac event" are used interchangeably and refer to both normal or abnormal events.

The terms "normal" and "sinus" are used to refer to events, features, and characteristics of, or appropriate to, a heart's healthy or normal functioning.

The terms "abnormal," or "arrhythmic" are used to refer to events, features, and characteristics of, or appropriate to, an un-healthy or abnormal functioning of the heart.

The term "real-time" refers to a time frame contemporaneous with a normal or abnormal episode occurrence. For example, a real-time process or operation would occur during or immediately after (e.g., within minutes or seconds after) a cardiac event, a series of cardiac events, an arrhythmia episode, and the like.

Figure 1A:
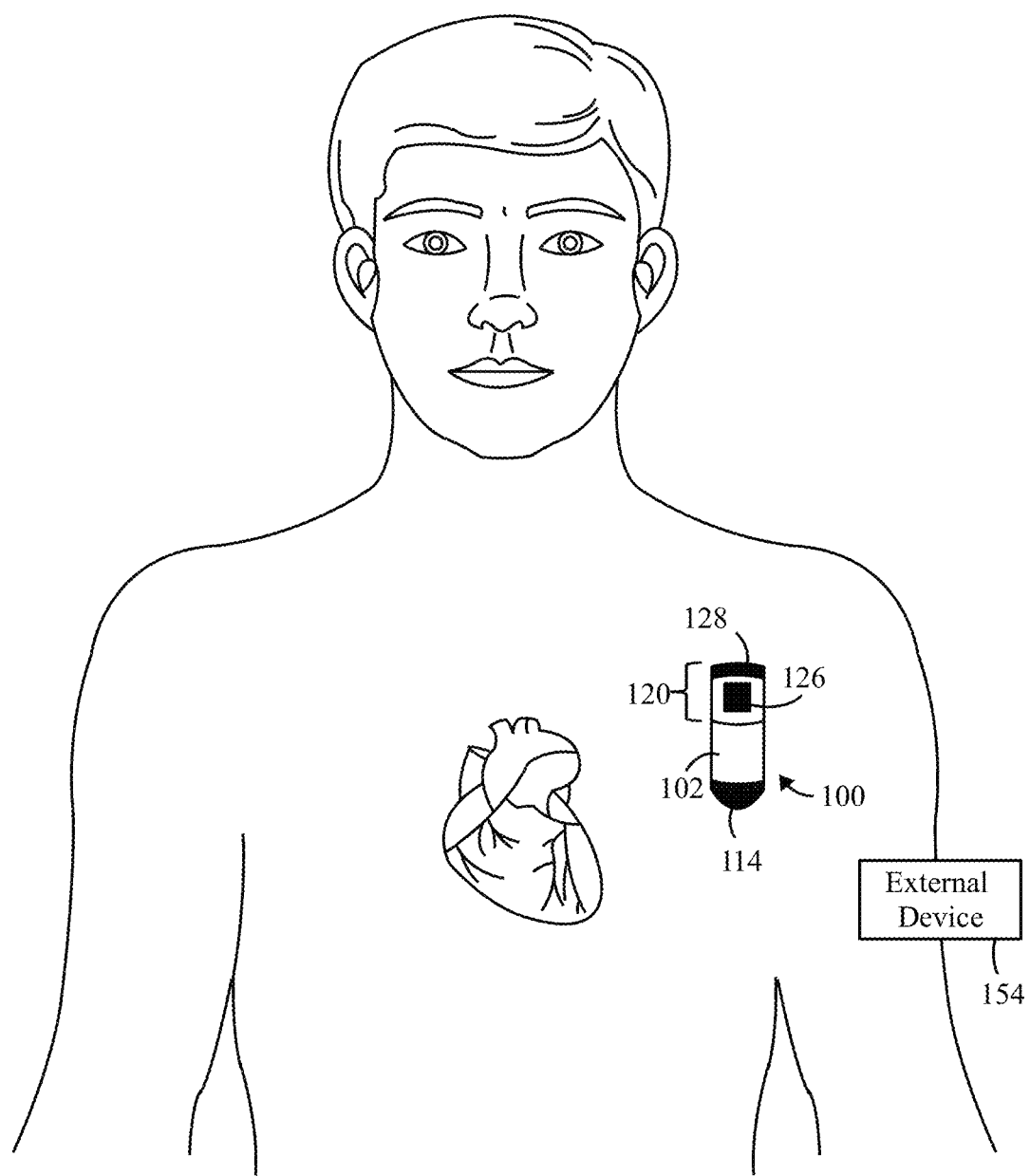
FIG. 1A illustrates an implantable cardiac monitoring device (ICM) intended for subcutaneous implantation at a site near the heart in accordance with embodiments herein.
Figure 1B:
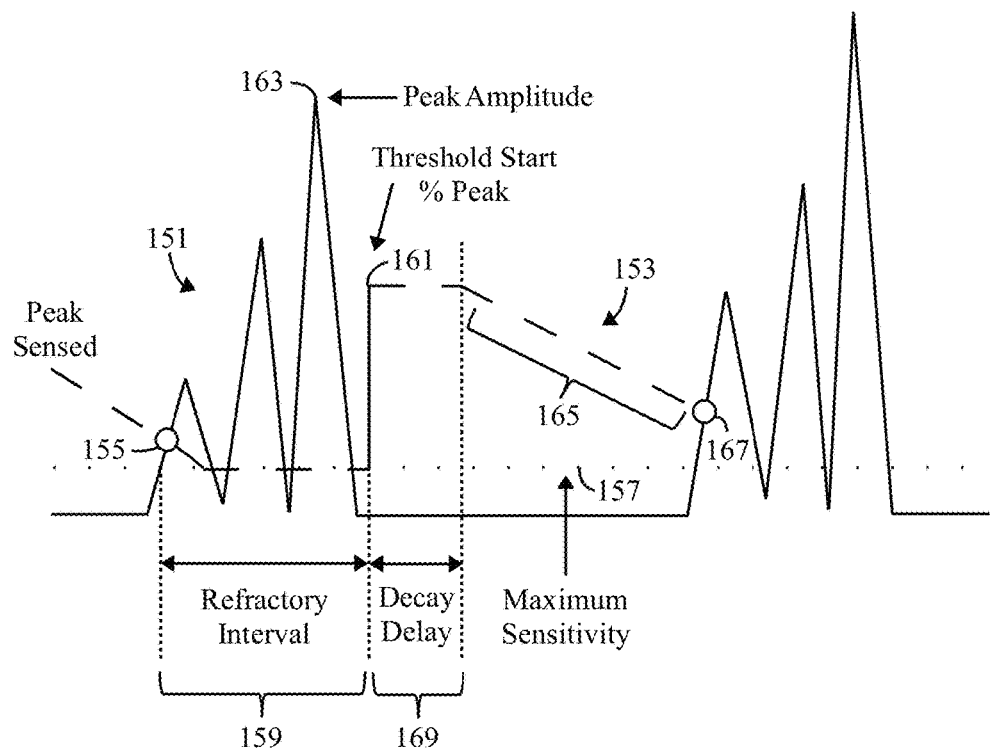
FIG. 1B illustrates a conventional sensitivity profile followed by an automatic sensing control (ASC) algorithm utilized by a conventional AF detection algorithm in accordance with embodiments herein.

FIG. 1A illustrates an implantable cardiac monitoring device (ICM) 100 intended for subcutaneous implantation at a site near the heart. The ICM 100 includes a pair of spaced-apart sense electrodes 114, 126 positioned with respect to a housing 102. The sense electrodes 114, 126 provide for detection of far field electrogram signals. Numerous configurations of electrode arrangements are possible. For example, the electrode 114 may be located on a distal end of the ICM 100, while the electrode 126 is located on a proximal side of the ICM 100. Additionally, or alternatively, electrodes 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the AF detection algorithm described herein, a loop memory for temporary storage of CA data, a device memory for long-term storage of CA data upon certain triggering events, such as AF detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor—tissue interface. The ICM 100 may be configured to be activated by the patient or automatically activated, in connection with recording subcutaneous ECG signals.

The ICM 100 senses far field, subcutaneous CA signals, processes the CA signals to detect arrhythmias and if an arrhythmia is detected, automatically records the CA signals in memory for subsequent transmission to an external device 154. The CA signal processing and arrhythmia detection is provided for, at least in part, by algorithms embodied in or implemented by the microprocessor. The ICM 100 includes one or more processors and memory that stores program instructions directing the processors to implement arrhythmia detection utilizing an on-board R-R interval irregularity (ORI) process that analyzes cardiac activity signals collected over one or more sensing channels.

Figure 2:
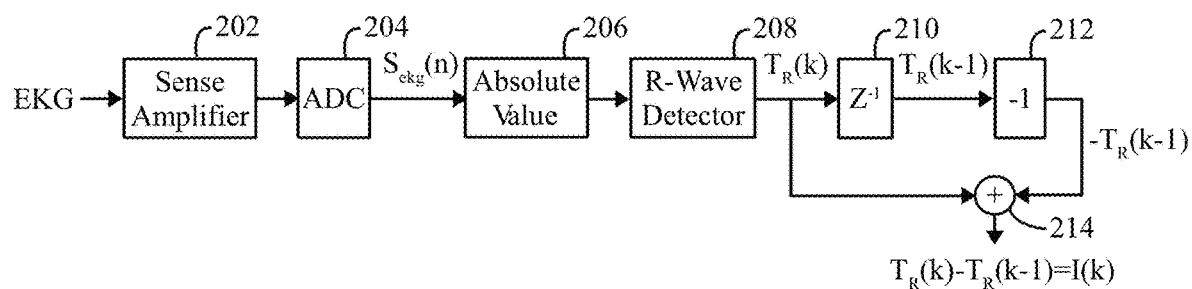
FIG. 2 illustrates a block diagram of a signal processing channel implemented in accordance with embodiments herein.

FIG. 2 illustrates a block diagram of a signal processing channel implemented in accordance with embodiments herein, to identify R-waves in CA signals. The process of FIG. 2 also identifies a time at which the R-waves occur, $T_R(k)$. An analog sense amplifier 202 is provided to generate CA signals based on cardiac activity sensed by a combination of active electrodes. The analog sense amplifier 202 outputs narrow band CA signals, thereby attempting to selectively pass R-waves while rejecting T-waves and noise. Although, the narrow band CA signals still may contain at least some T-waves and/or noise. The narrow band CA signals are digitized at an analog to digital converter (ADC) 204 utilizing a select sample frequency (e.g., at 128 to 512 Hertz) to yield digitized CA signals, $S_{ekg}(n)$. For computational efficiency the absolute value of sampled narrow band signal, $|S_{ekg}(n)|$, is obtained at 206. Next the CA signals are passed through an R-wave detector 208 implemented in accordance with embodiments herein. A time at which each R-wave occurs is identified (the time the R-wave occurred is time delayed a 210) and output as an R-wave incidence point $T_R(k)$. The R-wave incidence point is subtracted (at subtraction unit 214) from a prior R-wave incidence point $T_R(k-1)$ at which a prior R-wave occurred. The prior R-wave incidence point $T_R(k-1)$ is stored in a buffer 212. For example, the timer 210 may utilize a continuous timer that outputs an R-wave time stamp each time an R-wave is detected at the R-wave detector 208. The subtraction unit 214 subtracts the prior R-wave incidence point $T_R(k-1)$ from the current R-wave incidence point $T_R(k)$ to obtain an RR interval I(k). The RR intervals are then stored in a circular buffer and analyzed for irregularities in connection with declaring an arrhythmia.

Figure 4:
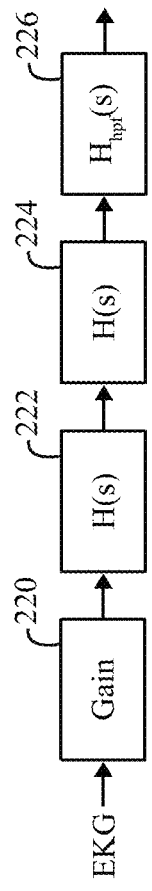
FIG. 4 illustrates a block diagram of a basic signal process, implemented in accordance with an alternatively embodiment herein.

FIG. 4 illustrates a block diagram of the sense amplifier 202 formed in accordance with embodiments herein. The sense amplifier 202 includes a gain circuit 220, followed by two analogue biquad amplifiers 222, 224 connected in series with a low pass filter 226. The functionality of the sense amplifier 202 can be represented in the frequency domain as shown below in equations EQ1 and EQ2.

$$H(s) = \frac{\frac{\omega_o}{Q} \cdot s}{s^2 + \frac{\omega_o}{Q} \cdot s + w_o^2} \qquad \text{EQ1}$$

$$H_{hpf}(s) = \frac{\frac{s}{\omega_L}}{\frac{s}{\omega_L} + 1} \qquad \text{EQ2}$$

Additionally, or alternatively, the digital sense filter of FIG. 4 and equations EQ1 and EQ2 may be modified to utilize a bilinear transform and convert the H(s) and $H_{hpf}(s)$ amplifiers into digital filters.

Figure 3:
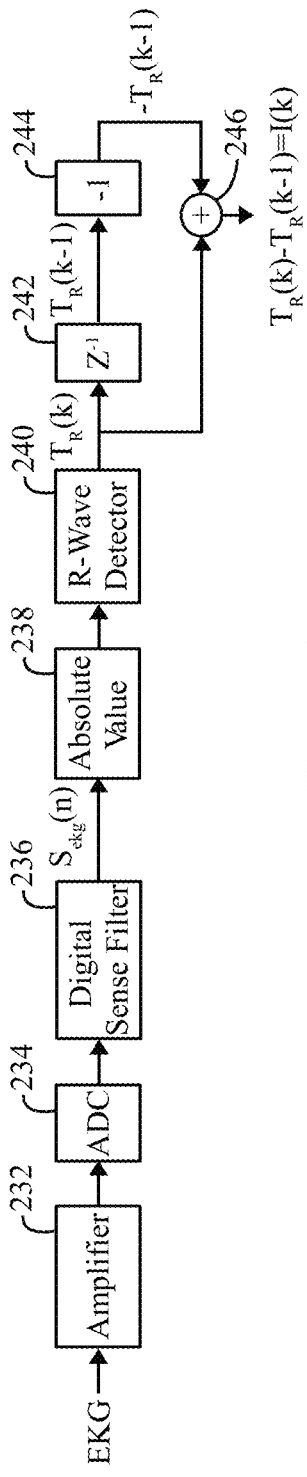
FIG. 3 illustrates a block diagram of the filtered sense amplifier channel formed in accordance with embodiments herein.

FIG. 3 illustrates a block diagram of a basic signal process, implemented in accordance with an alternatively embodiment herein, to identify R-waves in CA signals and a time at which the R-waves occur, $T_R(k)$. A wide band amplifier 232 is used to condition the signal for the analog to digital conversion process at ADC 234. The digitized CA signals are then processed by a digital filter 236 (or filters) to yield a sampled narrow band signal $S_{ekg}(n)$. An absolute value unit 238 rectifies the narrow band signal and the rectified signal is passed to an R-wave detector 240 implemented in accordance with embodiments herein. The R-wave detector 240 identifies the R-waves in the incoming CA signals, and an R-wave timer 242 identifies a time at which each R-wave occurs and outputs the time as $T_R(k)$. The current R-wave timing (or R-wave incidence point) is subtracted (at subtraction unit 246) from a time at which a preceding/prior R-wave incidence point $T_R(k-1)$. The preceding R-wave incidence point $T_R(k-1)$ is stored in a buffer 244. The subtraction unit 246 subtracts the prior R-wave incidence point $T_R(k-1)$ from the current R-wave incidence point $T_R(k)$ to obtain the RR interval I(k). The RR intervals between successive R waves are stored in a circular buffer and analyzed for irregularities in connection with declaring an arrhythmia.

Figure 5:
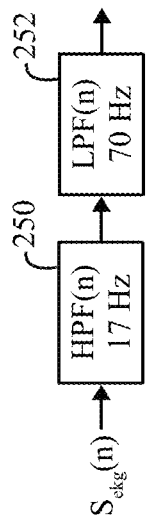
FIG. 5 illustrates a block diagram of the digital filter formed in accordance with embodiments herein.

FIG. 5 illustrates a block diagram of the digital filter 236 formed in accordance with embodiments herein. The digital filter 236 may be implemented using a high pass filter (HPF) 250 and a low pass filter (LPF) 252 coupled in series with one another. The digital filter 236 may be a first order high pass filter 250, HPF(n), passing signals greater than a select first frequency $f_l$ (e.g., below 20 Hz), followed by a low pass filter 252 at a select second frequency $f_h$ (e.g., 50 to 100 Hertz). For example, the HPF 250 and LFP 252 may implement equations EQ3 and EQ4, respectively, as set forth below.

$$HPF(n) = \frac{1}{1 + 2\pi f_l / f_s} \cdot [(HPR(n-1) + S_{in}(n) - S_{in}(n-1)] \qquad \text{EQ3}$$

$$LPF(n) = \frac{1}{1 + f_s/2\pi f_l} \cdot \left[ \frac{f_s}{2\pi f_h} LPF(n-1) + S_{in}(n) \right] \qquad \text{EQ4}$$

Figure 6:
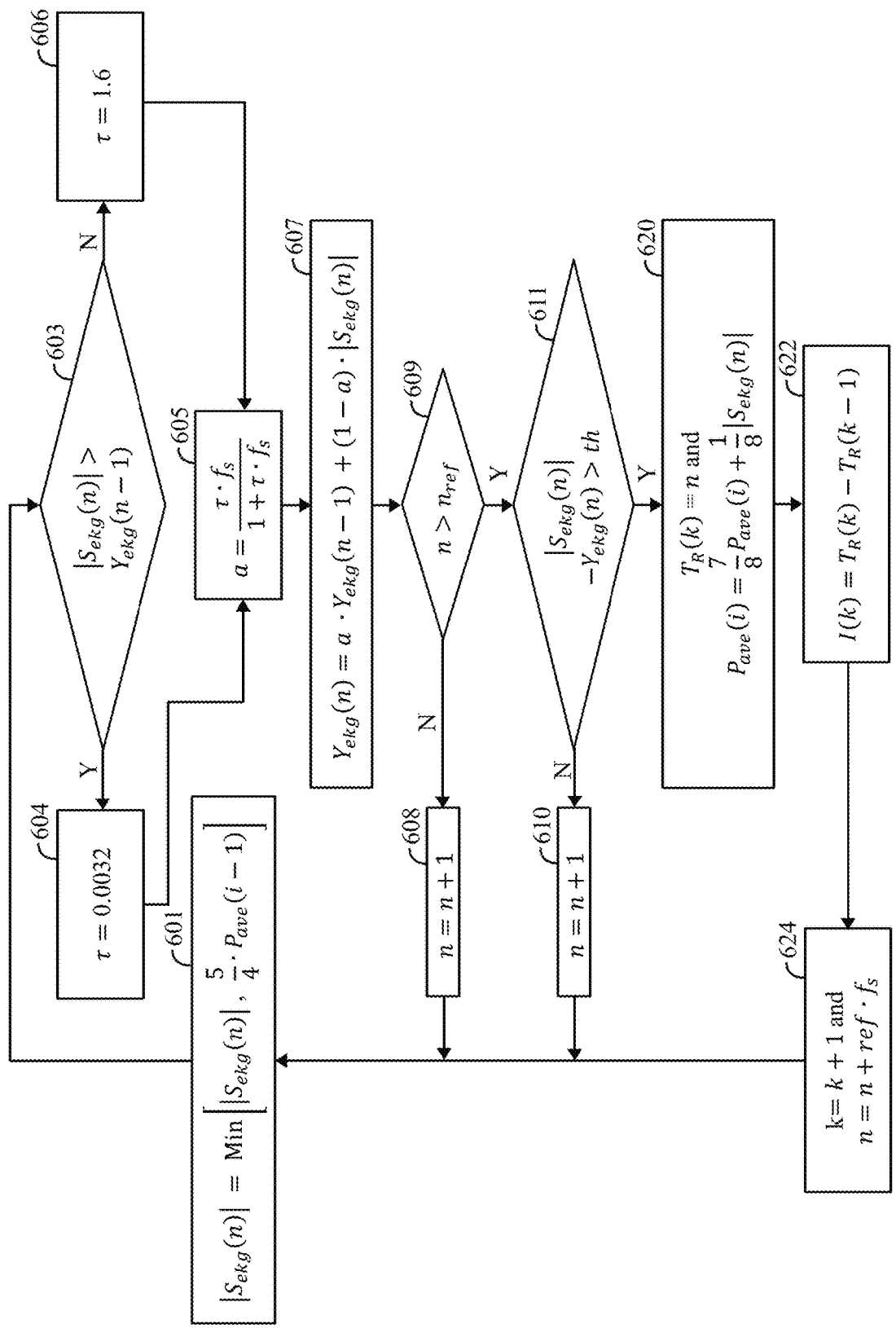
FIG. 6 illustrates a process for detecting R-waves in accordance with embodiments herein.

FIG. 6 illustrates a process for detecting R-waves in accordance with embodiments herein. The process of FIG. 6 may be performed by firmware, hardware, and other circuits within an ICM. Additionally, or alternatively, all or a portion of the process of FIG. 6 may be performed by a local external device and/or a remote server. As explained herein, the process of FIG. 6 applies a direction related responsiveness (DRR) filter to the CA signals to form DRR filtered CA signals that are analyzed to identify R waves in the CA signals. A responsiveness of the DRR filter varies based on, and in connection with, changes in an amplitude of the CA signals (as determined by the adjusted CA value). The responsiveness of the DRR filter is direction related, in a "Fast Up Slow Down" manner, as the DRR filter exhibits fast responsiveness when the CA signal is increasing (e.g., exhibits an increasing trend/slope) and the DRR filter exhibits slow responsiveness when the CA signal is decreasing (e.g., exhibits a decreasing trend/slope). The terms fast and slow do not represent a particular speed, but instead are merely used relative to one another to indicate differences in the filter response for increasing and decreasing CA signals.

At 601, the one or more processors obtain a data sample from the CA signals. The data sample is rectified and thus represents an absolute value $|S_{ekg}(n)|$ of the CA signal $S_{ekg}$ at the corresponding sample index (n). At 601, the processors determine which is lower (e.g., a minimum), the current CA signal sample or a running CA signal average $P_{ave}(i-1)$ that is maintained as explained herein. The processors select the lower/minimum of the current CA signal sample and the running average as an adjusted CA value $S_{ekg}(n)$. The adjusted CA value is also referred to as the current sample of the CA signals in connection with the operations of FIG. 6. The running CA signal average $P_{ave}(i-1)$ is computed at 620 as discussed below. The operation at 601 avoids setting a very high CA signal value for a start of an estimation of the DRR filtered signals $Y_{ekg}(n)$. An excessive value for the current CA signal sample $|S_{egk}(n)|$ may be caused by an ectopic beat, such as a premature ventricular contraction (PVC). If left uncorrected, an overly high CA signal sample may cause the DRR filtered signals to remain excessively high as well such that a next R-wave will not be detected at 611.

At 603, the one or more processors compare an amplitude of the current sample from the adjusted CA signals $|S_{ekg}(n)|$ to an amplitude of a preceding sample from the DRR filtered signals $Y_{ekg}(n-1)$ to identify a direction characteristic of the CA signals. The direction characteristic represents an increasing trend in the CA signals or a decreasing trend in the CA signals relative to the prior sample of the DRR filtered signals. The processors define a filter coefficient of the DRR filter based on a time constant that is set based on the direction characteristic identified. For example, when the comparison/test indicates that the current adjusted CA sample is greater than the prior sample from the DRR filtered signals $|S_{ekg}(n)|>Y_{ekg}(n-1)$, flow branches to 604 where the processors set a relatively short time constant for the DRR filter (e.g., $\tau=0.0025$ to 0.004). The short time constant is then used by the DRR filter at 607, such that an output of the DRR filter rapidly responds to increases in the incoming CA signals. Conversely, when the test indicates that $|S_{ekg}(n)| \leq Y_{ekg}(n-1)$, flow branches to 604 where the processors set a relatively long time constant for the DRR filter (e.g., T=1.2 to 2.2).

At 605, the one or more processors define a filter coefficient "a" based on the time constant set at 604 or 606. For example, the filter coefficient may be defined based on the following equation: $a=(\tau*f_s)/(1+\tau*f_s)$, where $f_s$ represents the sample rate and $\tau$ represents the time constant set at 604 or 606.

At 607, the one or more processors apply a DRR filter to the rectified CA signals to produce DRR filtered signals. For example, the processors use the DRR filter to compute a new value of the DRR filtered signals, $Y_{ekg}(n)$ using the latest sampled absolute value of the adjusted CA signals $|S_{ekg}(n)|$ and the stored prior sample of the DRR filtered signals, $Y_{ekg}(n-1)$. A long time constant (at 606) is used by the DRR filter to respond to decreases, in the incoming CA signals, more slowly as compared to the responsiveness of the DRR filter to increases in the incoming CA signals (which uses a short time constant set at 604). By way of example, the DRR filter may use the following equation to calculate the next DRR filtered signals: $Y_{ekg}(n)=a \cdot Y_{ekg}(n-1)+(1-a) \cdot |S_{ekg}(n)|$, where "a" is calculated at 605 based on the time constant set at 604 or 606. The test at 611 avoids a need to finding a new peak for a refractory period, ref that is computed in 046.

At 609, the one or more processors determine whether the sample index n is greater than the refractory sample index $n_{ref}$. If so, the process continues to 611. Otherwise, the process moves to 608. At 608, the one or more processors increment the sample index to the next sample in the stream of CA signal samples (e.g., n=n+1).

At 611, the one or more processors analyze the adjusted CA signal sample at the sample index n to detect for an R-wave. For example, the processors calculate a difference between amplitudes of the adjusted/current CA signal sample and the prior sample of the DRR filtered signals, and determine whether the difference exceeds a threshold (e.g., if $|S_{ekg}(n)|-Y_{ekg}(n)>th$). When the amplitude difference exceeds the threshold, the processors interpret the condition to represent detection of a peak of an R-wave. When the difference threshold is exceeded and an R-wave peak is detected, flow moves to 620. Alternatively, when the amplitude difference does not exceed the threshold, the processors interpret the condition to represent absence of R-wave peak and flow branches to 610. At 610, the one or more processors increment the sample index to the next sample in the stream of CA signal samples (e.g., n=n+1).

At 620, the one or more processors determine a point in time at which a peak of the R-wave was detected at 620. The point in time is referred to as an R-wave incidence point. When an R-wave peak is identified at 620, the R-wave incidence point corresponds to a current value for the sample index (n). The R-wave incidence point is stored in a buffer as a current R-wave incidence point $T_R(k)=n$, where $T_R$ represents a time/index of an R-wave peak and (k) represents the $k_{th}$ R-wave sample peak. At 620, the processors also compute the running average of the approximate peak value of the CA signals $|S_{ekg}(n)|$ that is detected by 611. The CA signal running average of the peaks $(P_{ave})$ is computed each time a peak R-wave is detected at 611. The value of the CA signal running average of the $i_{th}$ value of $P_{ave}(i)$ is stored in memory.

Figure 7:
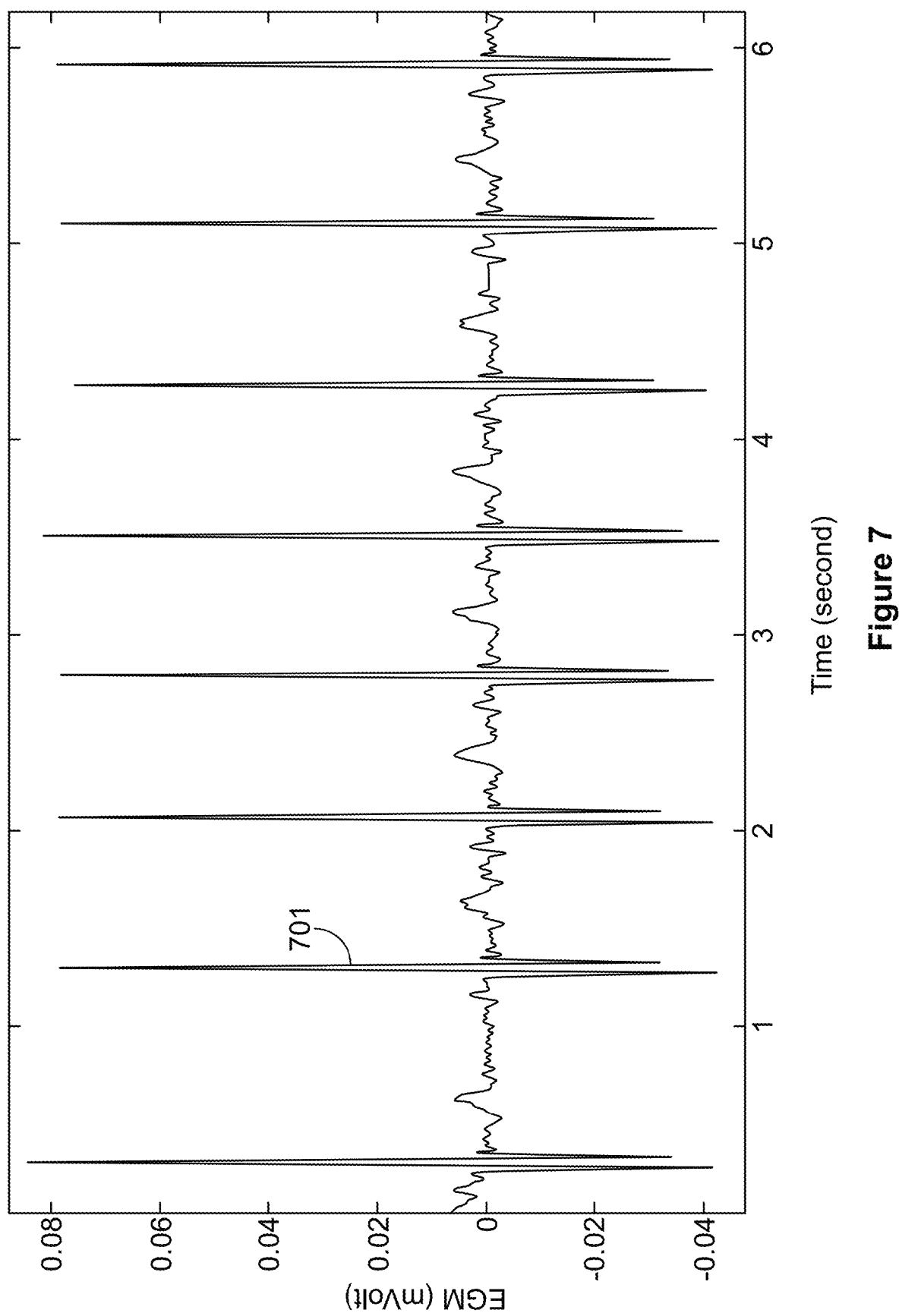
FIG. 7 illustrates a graphical representation of CA signals over time in accordance with embodiments herein.

FIGS. 7-11 illustrate examples of the signals processed at 601-607. FIG. 7 illustrates a graphical representation of CA signals 701 over time. For example, the CA signals may represent a subcutaneous EKG signal such as collected by an ICM or a subcutaneous implantable cardiac defibrillator (Sub-Q ICD).

Figure 8:
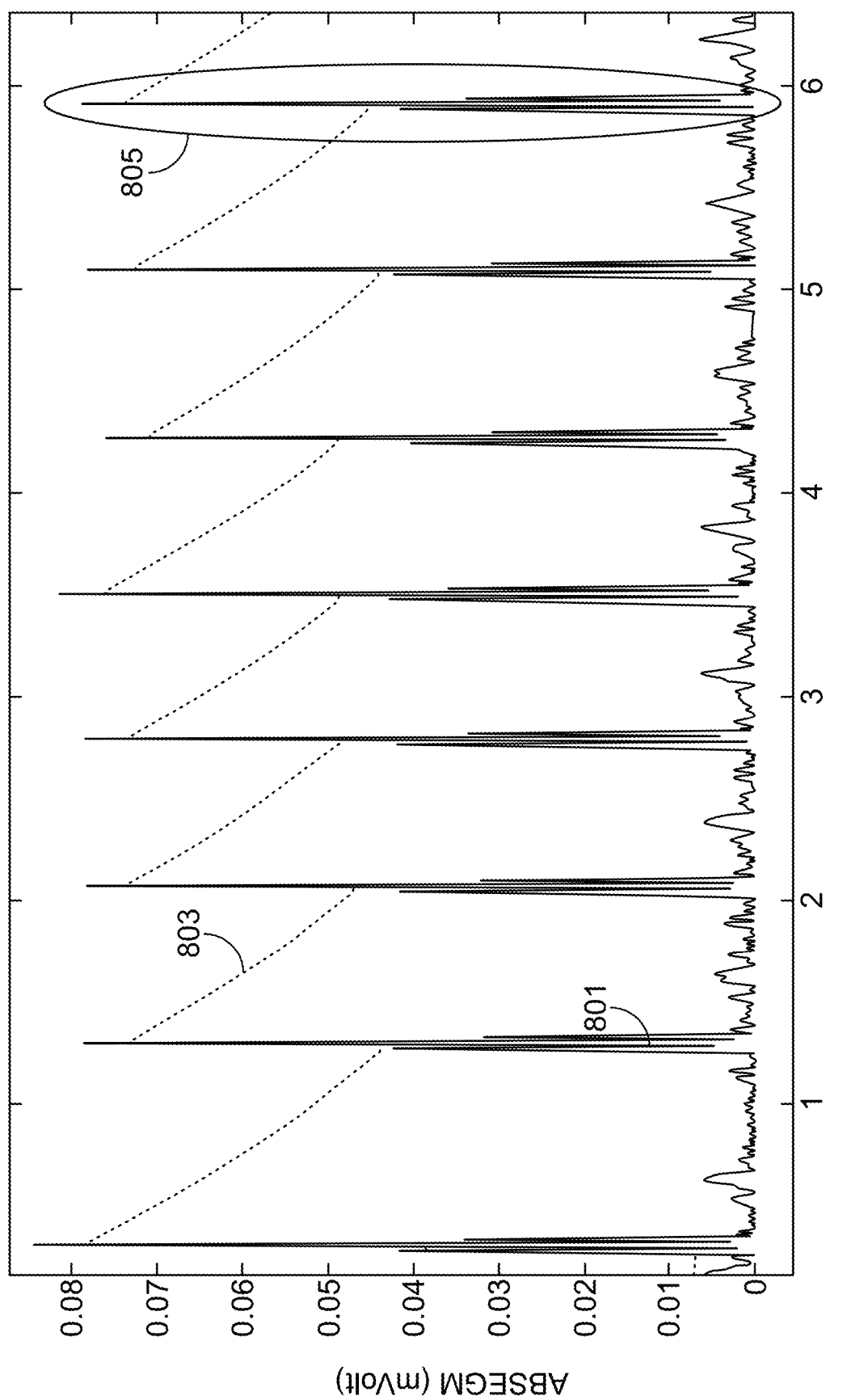
FIG. 8 illustrates adjusted CA signals, such as a rectified CA signal or absolute value $|(S_{ekg}(n)|$ in accordance with embodiments herein.

FIG. 8 illustrates adjusted CA signals, such as a rectified CA signal or absolute value $|S_{ekg}(n)|$, labelled as 801. The adjusted CA signals are processed as described herein at 607 (and at 206, 238 in FIGS. 2 and 3) to form a DRR filtered signals denoted at 803. The DRR filtered signals 803 represent the "Fast Up Slow Down Filter" output $Y_{ekg}(n)$ at sample index (n).

Figure 9:
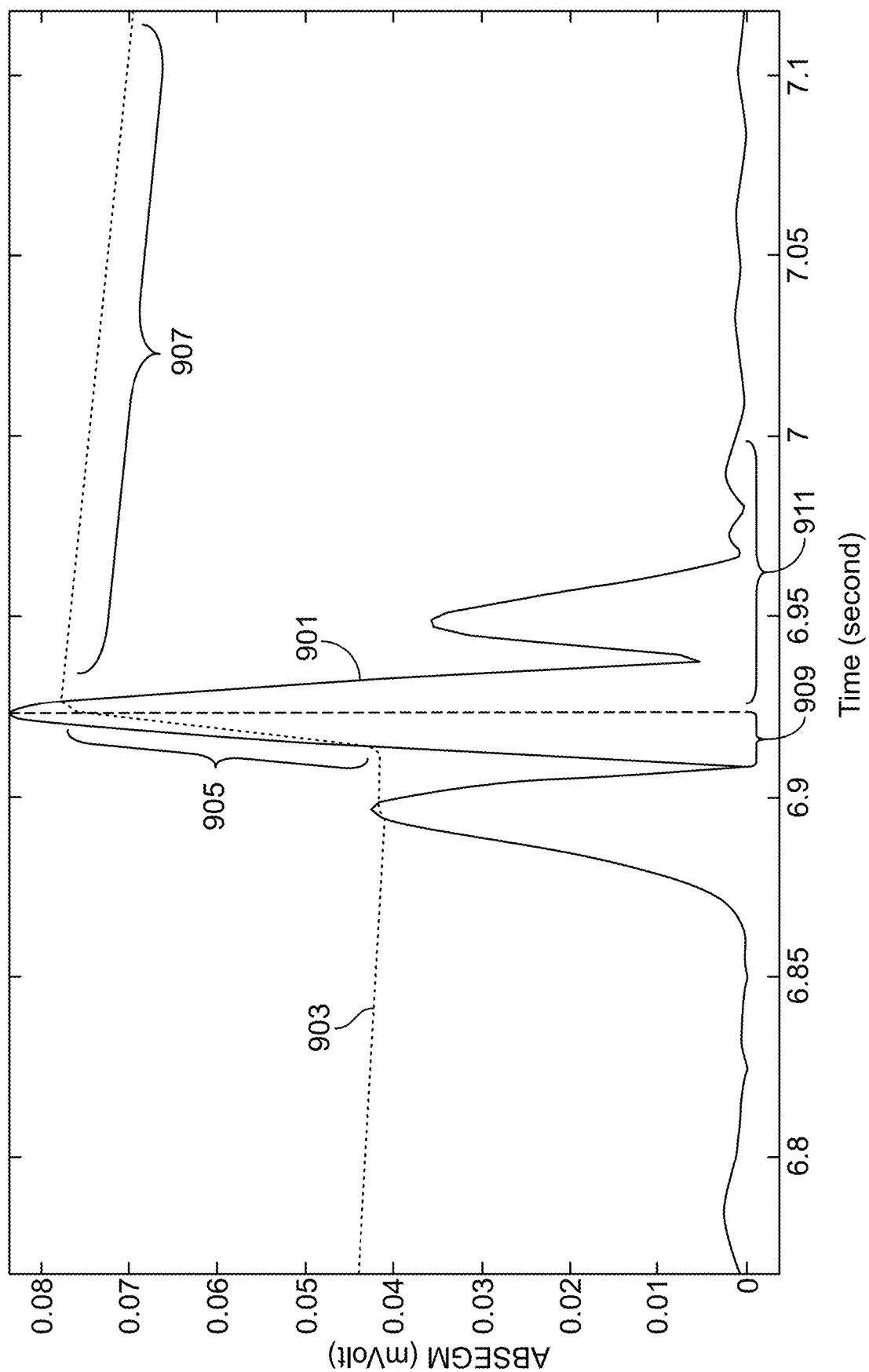
FIG. 9 illustrates a magnified version of an R-wave portion of the rectified adjusted CA signals that is circled in FIG. 8 in accordance with embodiments herein.

FIG. 9 illustrates a magnified version of an R-wave portion of the rectified adjusted CA signals that is circled in FIG. 8 and labelled 805. The signal labeled 901 represents a magnified peak of the rectified R-wave $|S_{ekg}(n)|$. The DRR filtered signals 903 is also magnified to illustrate the "Fast Up Slow Down Filter" behavior $Y_{ekg}(n)$. The DRR filtered signals 903 includes a rising filtered segment 905 and a decreasing filtered segment 907. The increasing segment 905 exhibits an upward slope that increases at a rate that is substantially similar to a rate at which the R-wave 901 increases at rising segment 909. The decreasing filtered segment 907 exhibits a downward slope that is substantially slower/lower than a rate at which the R-wave 901 decreases along the trailing segment 911. As explained above in connection with 603-606, the process of FIG. 6 identifies the rising segment 909 of the R-wave 901 and defines a filter response to have a fast time constant to produce the rising filtered segment 905 during the rising segment 909. The process of FIG. 6 identifies the trailing segment 911 of the R-wave 901 and defines a filter response to have a slow time constant to produce the decreasing filtered segment 907 during the trailing segment 911.

Figure 10:
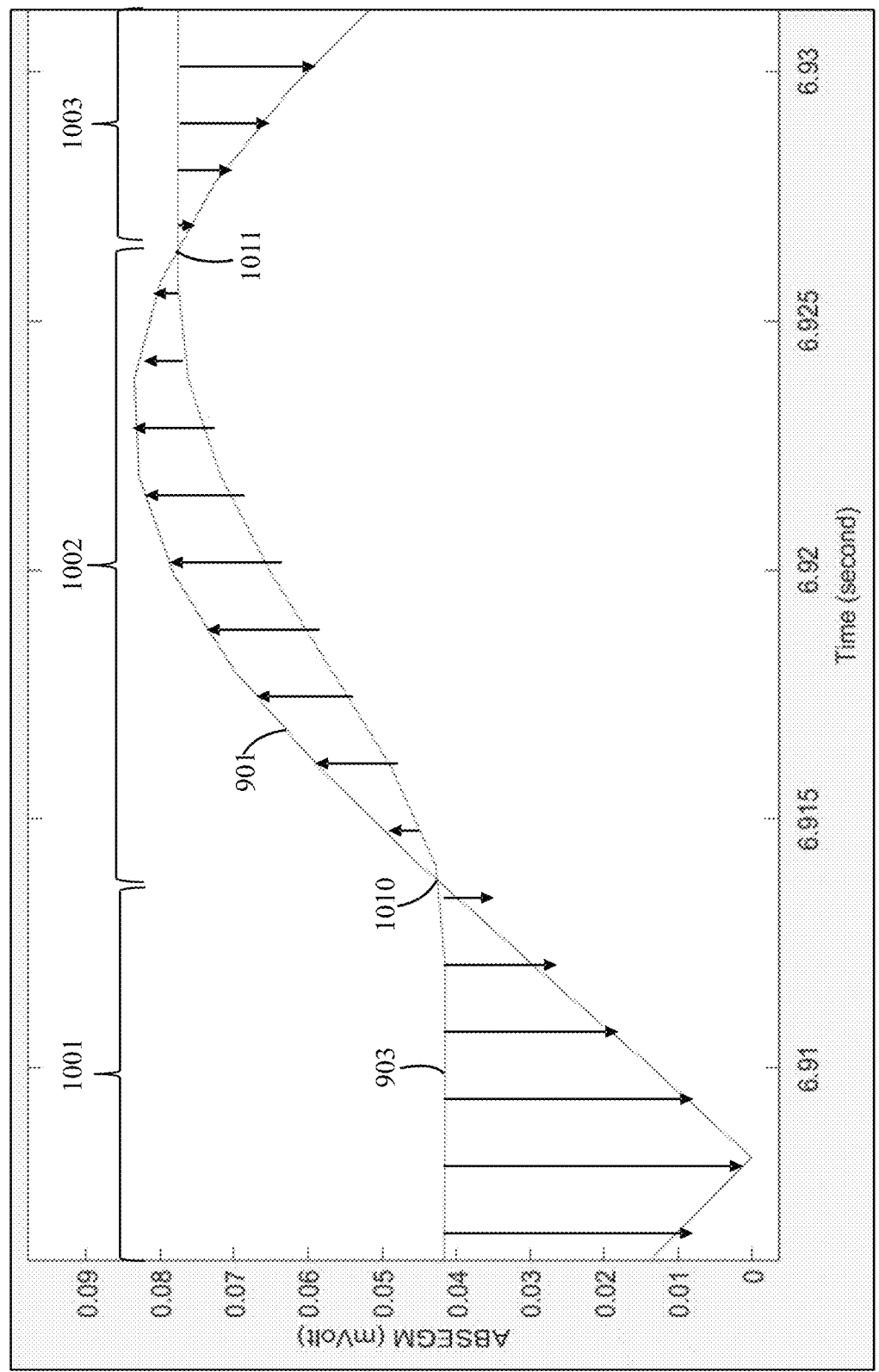
FIG. 10 illustrates an enlarged view of a peak of the R-wave of FIG. 9 in accordance with embodiments herein.

FIG. 10 illustrates an enlarged view of a peak of the R-wave of FIG. 9. In FIG. 10, the adjusted/rectified CA signal 901 and the DRR filtered signal 903 cross one another at points 1010 and 1011. A series of downward arrows are illustrated in ranges 1001 and 1003 to show where the rectified R-wave is less than or equal to the DRR filtered signals, while the upward arrows 1002 show where the R-wave is greater than the DRR filtered signals. The process of FIG. 6 applies a "greater than" condition test at 611 for, $|S_{ekg}(n)|-Y_{ekg}(n)>th$ and when the condition is satisfied, the event is deemed to be a bona fide R-wave. In the example of FIG. 10, the condition would be satisfied during the range 1002.

Figure 11:
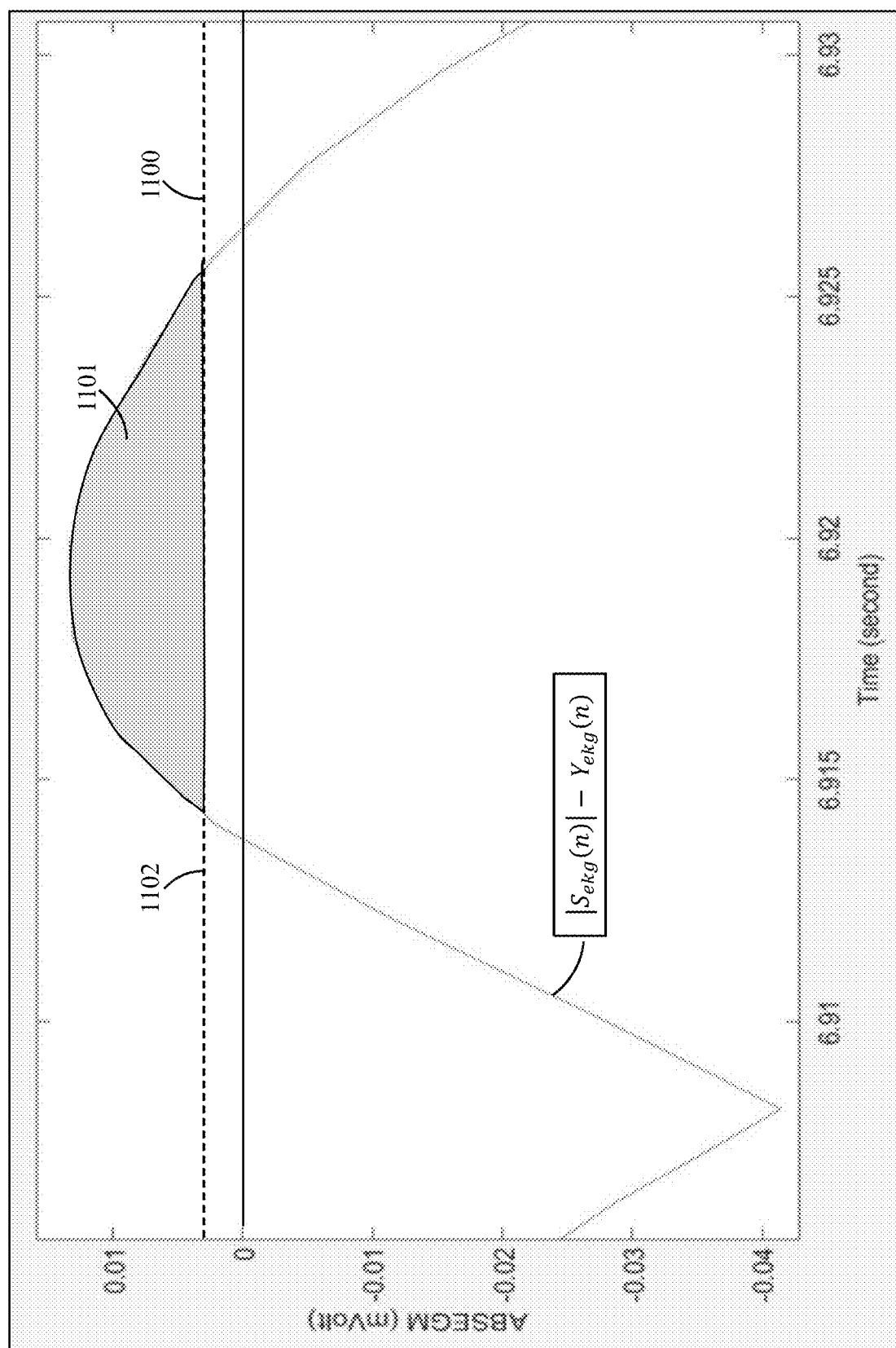
FIG. 11 illustrates a difference between the adjusted CA signals $|S_{ekg}(n)|$ and the direction related responsiveness (DRR) filtered signals $Y_{ekg}(n)$ at a series of samples (n) in accordance with embodiments herein.

FIG. 11 illustrates a difference between the adjusted CA signals $|S_{ekg}(n)|$ and the DRR filtered signals $Y_{ekg}(n)$ at a series of samples (n). FIG. 11 also illustrates a threshold (th) 1100, 1102 utilized during the R-wave detection test at 611. A cross-hatched area 1101 shows where the difference is greater than the threshold th. The processors interpret this condition to indicate an R-wave has occurred.

Returning to FIG. 6, at 622, the one or more processors compute the most recent R-wave to R-wave interval, I(k) by subtracting a previously stored R-wave incidence point $T_R(k-1)$ from a current R-wave incidence point $T_R(k)$. The processors store a series of RR intervals (e.g., 4 to about 64 RR intervals) in a circular buffer that is managed as a first-in first-out buffer where the oldest RR interval is written over with the current RR interval. The RR intervals in the circular buffer are analyzed in accordance with various arrhythmia detection algorithms, such as to search for AF events. By way of example, the RR intervals in the circular buffer may be analyzed as (described herein) in connection with the on-board RR interval irregularity (ORI) process, a first pass AF detection process, a second pass AF detection process and the like. As a further example, the RR intervals may be analyzed by AF detection algorithms described in U.S. Pat. No. 8,135,456, the complete subject matter of which is incorporated herein by reference.

At 624, the one or more processors increment an RR interval counter k by one (k=k+1) and step the analysis process forward along the stream of CA signal samples by a number of samples equal to the refractory interval. For example, at 624 the processors step, a sample index $n_{ref}$ forward for the next CA signal sample to be analyzed, where $n_{ref}$ is calculated using the equation: $n_{ref}=n+ref*f_s$. By way of example, the processors add the number of intervals=$ref \cdot f_s$ to the current sample index n. The term, ref, refers to a duration of a refractory period following R-wave detection, during which the processors do not search for R-waves. By way of example, refractory period, ref, may be set to between about 0.1 to 0.25 seconds. The product of the duration of the refractory period and the sample frequency (ref*$f_s$) provides the number of samples that occur during the refractory period.

The process at 601-624 is repeated while stepping through a series of CA signal samples to identify R-waves, calculate RR intervals and load the RR intervals into the circular buffer.

Figure 12:
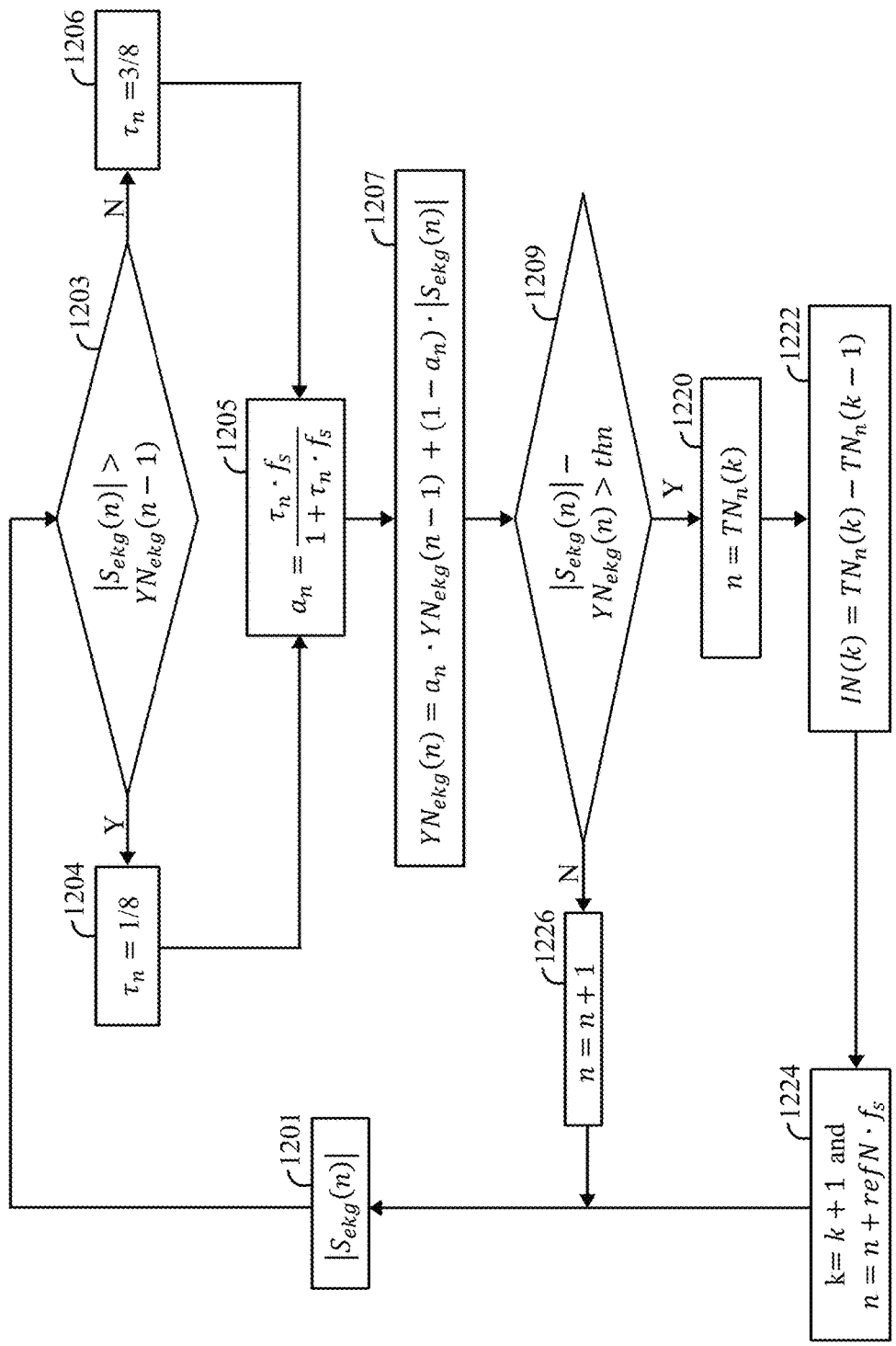
FIG. 12 illustrates a process for detecting noise in CA signals in accordance with an alternative embodiment.

FIG. 12 illustrates a process for detecting noise in CA signals in accordance with an alternative embodiment. The process of FIG. 12 may be performed by firmware, hardware, and other circuits within the IMD. Additionally, or alternatively, all or a portion of the process of FIG. 6 may be performed by a local external device and/or a remote server. Noise caused by myopotentials may corrupt an ECG strip and render accurate R-wave detection difficult. When myopotentials occur, embodiments herein identify the noise and determine whether to ignore the noisy segment of CA signals in order to eliminate the possibility of a false ventricular fibrillation (VF) or ventricular tachycardia (VT) detection.

At 1201, the one or more processors obtain a data sample from the CA signals. The data sample is rectified and thus represents an absolute value $|S_{ekg}(n)|$ of the CA signal $S_{ekg}$ at the corresponding sample index (n).

At 1203, the one or more processors compare an amplitude of the current adjusted CA value $|S_{ekg}(n)|$ to an amplitude of a preceding (potentially noisy) DRR filtered signals $YN_{ekg}(n-1)$, and sets a time constant utilized by the DRR filter based on the comparison. For example, when the test indicates that the current adjusted CA value is greater than the preceding DRR filtered signals $|S_{ekg}(n)|>YN_{ekg}(n-1)$, flow branches to 1204 where the processors set a relatively short noise related time constant for the DRR filter (e.g., $\tau=\frac{1}{8}$). The short noise related time constant is then used by the DRR filter at 1207, such that an output of the DRR filter rapidly responds to increases in the incoming CA signals associated with noise. Conversely, when the test indicates that $|S_{ekg}(n)|<=YN_{ekg}(n-1)$, flow branches to 1204 where the processors set a relatively long noise related time constant for the DRR filter (e.g., $\tau=\frac{3}{8}$). The time constants are "noise related" as the time constants are defined based on characteristics of noise.

At 1205, the one or more processors define a noise filter coefficient "$a_n$" based on the noise related time constant set at 1204 or 1206. For example, the noise filter coefficient may be defined based on the following equation: $a_n=(\tau_n*f_s)/(1+\tau_n*f_s)$, where $f_s$ represents the sample rate and $\tau_n$ represents the noise adjusted time constant set at 1204 or 1206.

At 1207, the one or more processors use the DRR filter to compute a new value of the DRR filtered signals, $YN_{ekg}(n)$ using the latest sampled absolute value of the adjusted CA signals $|S_{ekg}(n)|$ and the stored prior sample of the DRR filtered signals, $YN_{ekg}(n-1)$. A long time constant (at 1206) is used by the DRR filter to respond to decreases, in the incoming CA signals, more slowly as compared to the responsiveness of the DRR filter to increases in the incoming CA signals (which uses a short time constant set at 1204). By way of example, the DRR filter may use the following equation to calculate the next DRR filtered signals: $YN_{ekg}(n)=a_n*YN_{ekg}(n-1)+(1-a)*|S_{ekg}(n)|$, where "$a_n$" is calculated at 1205 based on the time constant set at 1204 or 12606.

At 1209, the one or more processors analyze the adjusted CA signal sample at the sample index n to detect for a noise peak. For example, the processors determine whether a difference between amplitudes of the current sample of the adjusted CA signal sample and the prior sample of the DRR filtered signals value exceed a threshold (e.g., if $|S_{ekg}(n)|-YN_{ekg}(n)>thn$). When the amplitude difference exceeds the threshold, the processors interpret the condition to represent detection of a noise peak. When the difference threshold is exceeded and a noise peak is detected, flow moves to 1220. Alternatively, when the amplitude difference does not exceed the threshold, the processors interpret the condition to represent detection of a non-noise peak and flow branches to 1226. At 1226, the one or more processors increment the sample index to the next sample in the stream of CA signal samples (e.g., n=n+1).

At 1220, the one or more processors store the discrete time, n, of the noise peak, $n=TN_n(k)$ as the $k_{th}$ sample of $TN_n(k)$. The point in time is referred to as a noise peak incidence point. When a noise peak is identified at 1220, the noise peak incidence point corresponds to a current value for the sample index (n). The noise peak incidence point is stored in a buffer as a current noise peak incidence point $TN_R(k)=n$, where $TN_R$ represents a time/index of a noise peak and (k) represents the km sample noise peak.

At 1222, the one or more processors subtract a previously stored discrete time of noise peak incidence point $TN_R(k-1)$ from $TN_R(k)$ to compute the most recent noise peak to noise peak interval, IN(k). The processors store a series of noise peak to peak (NPP) intervals (e.g., 4 to about 64 NPP intervals) in a circular buffer that is managed as a first-in first-out buffer where the oldest NPP interval is written over with the current NPP interval. The NPP intervals in the circular buffer are analyzed in accordance with various noise detection algorithms that determine whether there is noise. For example, noise may be declared when the NPP interval is below a minimum threshold (e.g., 200 ms). If X intervals out of the Y intervals are shorter than 200 ms, then the processors may declare a current segment of the CA signals to include excessive noise. When a current segment is declared to include excessive noise, the processors may discard/remove/label a select segment of the CA signals to form noise corrected CA signals. For example, the processors may remove a select segment (e.g., 1 or more seconds or y samples or z beats) of the CA signals that precedes the point at which noise was declared and remove a select segment of the CA signals that follows the point at which noise was declared to form the noise corrected CA signals. Optionally, a segment having excess noise may be ignored and/or the process may inhibit arrhythmia detection while noise is ongoing. Once arrhythmia detection is inhibited, the processors may search for one or more current segments that do not exhibit excessive noise and in response thereto turn back on arrhythmia detection. In some instances, the noise is often not removable because it is so severe and cannot be filtered out by a conventional linear filter because the noise is in a common frequency range. When the process is implemented in an ICM (e.g., not a therapeutic device), it may be desirable to ignore the noisy segments to avoid false positives and wait until new CA signals are relatively noise free in order that an arrhythmia can be detected with high confidence.

In accordance with embodiments herein, the operations provide a "loop recorder" device that allows for time delaying the analysis so that noise may first be recognized prior to trying to detect R-waves. Thus a current segment that includes excessive noise can be rejected in real time and the R-wave detection "turning off" in connection with the current "noisy" segment, thereby avoid confounding the R-wave detection algorithms. By rejecting noisy segments, embodiments herein avoid corruption of the R-wave detection algorithm outputs with false positive arrhythmic events. Avoiding false positive arrhythmic events, assists clinicians when trying to interpret monitoring outputs.

At 1224, the one or more processors set a refractory interval using the equation: $n_{ref}=n+refN \cdot f_s$. The foregoing equation represents adding a number of intervals=$refN \cdot f_s$ to the current interval, n. The term, refN, refers to a refractory period following detection of an event that may be noise. The value of refN may be between about 0.1 and 0.4 seconds. The product of $refN \cdot f_s$ represents the number of samples that occur during the refractory period, refN seconds.

Figure 13:
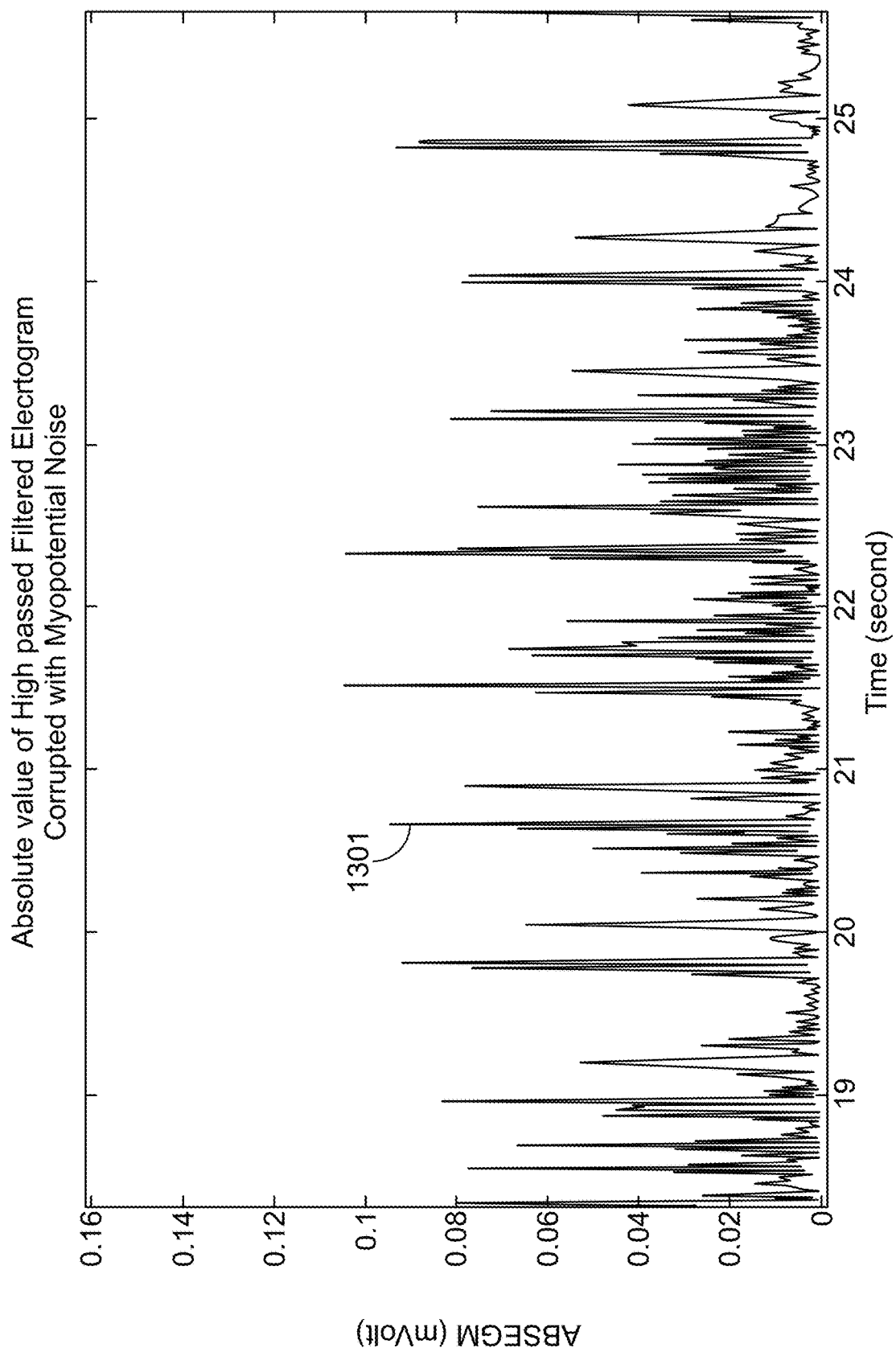
FIG. 13 illustrates examples of the signals processed in accordance with the operations of FIG. 12 in accordance with embodiments herein.
Figure 14:
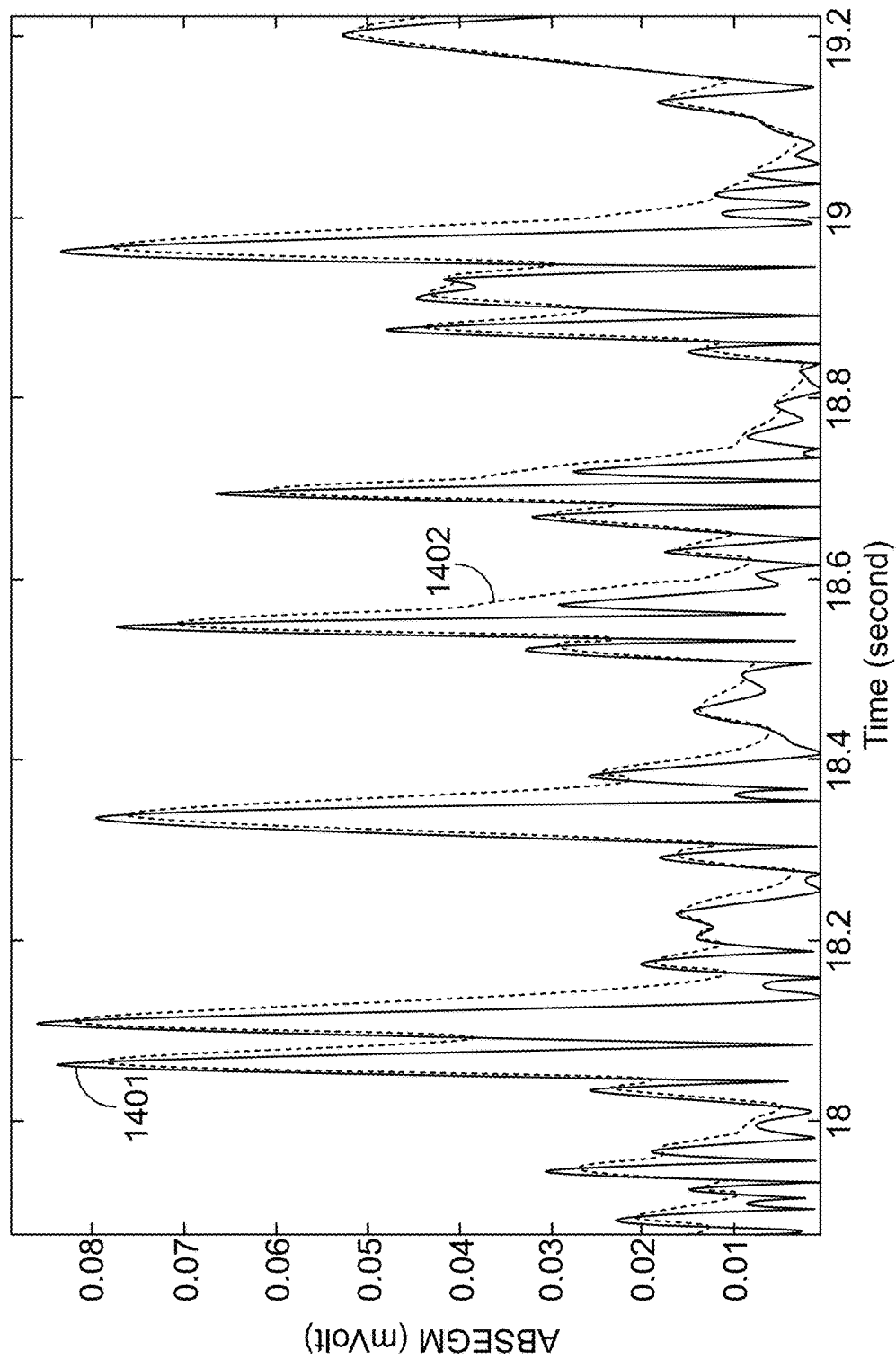
FIG. 14 illustrates examples of the signals processed in accordance with the operations of FIG. 12 in accordance with embodiments herein.
Figure 15:
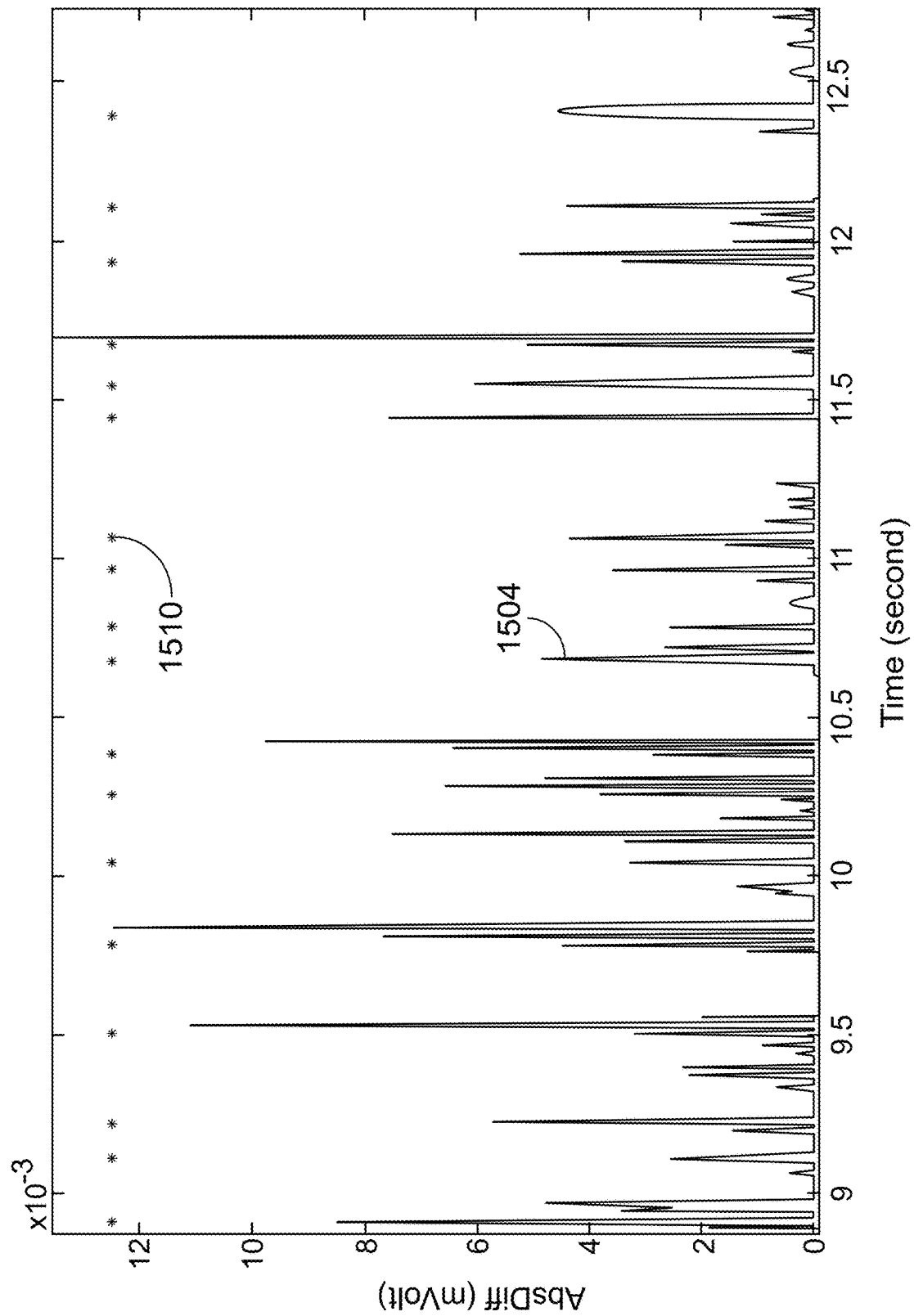
FIG. 15 illustrates examples of the signals processed in accordance with the operations of FIG. 12 in accordance with embodiments herein.

FIGS. 13-15 illustrate examples of the signals processed in accordance with the operations of FIG. 12. FIG. 13 illustrates a graphical representation of CA signals 1301 $|S_{ekg}(n)|$ corrupted with myopotential noise. FIG. 14 illustrates the CA signals $|S_{ekg}(n)|$, 1401, corrupted with myopotential noise overlaid with the DDR filter output, $YN_{ekg}(n)$, 1402, using the $\tau_n=\frac{1}{8}$ fast and $\tau_n=\frac{3}{8}$ slow noise related time constants.

FIG. 15 illustrates an absolute difference (AbsDiff) function 1504 that is defined as follows: if $|S_{ekg}(n)|-YN_{ekg}(n)>0$ then $AbsDiff=|S_{ekg}(n)|-YN_{ekg}(n)$; else $AbsDiff=0$. FIG. 15 also illustrates noise peak times 1510 that are marked as asterisks. The kth noise peak is defined at discrete time $n=TN_n(k)$ when $|S_{ekg}(n)|-YN_{ekg}(n)>thn$ as determined at 1209 of FIG. 12.

The operations of FIG. 12 are implemented upon CA signals to detect noise and remove segments of the CA signals that are unduly noisy. The operations of FIG. 12 may be implemented before the R-wave detection process of FIG. 6, where the process of FIG. 6 then performs R-wave detection upon the portion of the CA signals that remains after noisy segments have been removed in connection with the operations of FIG. 12. Additionally, or alternatively, the operations of FIG. 12 may be performed in parallel with or after the operations of FIG. 6. When an excessive amount of noise identified, the operations of FIG. 6 may be repeated and/or analyzed in other manners, such as in connection with a second pass confirmation.

Optionally, the operations of FIG. 6 may be implemented in connection with at least one of i) an arrhythmia first pass detection process or ii) an arrhythmia second pass confirmation process. Optionally, the operations of FIG. 12 may be implemented in connection with at least one of i) a noise first pass detection process or ii) a noise second pass confirmation process.

The operations of FIGS. 6 and/or 12 may be implemented by an implantable medical device housing the one or more processors. Additionally, or alternatively, the operations of FIGS. 6 and/or 12 may be implemented by one or more processors that are housed within at least one of a local external device and a remote server.

Figure 16A:
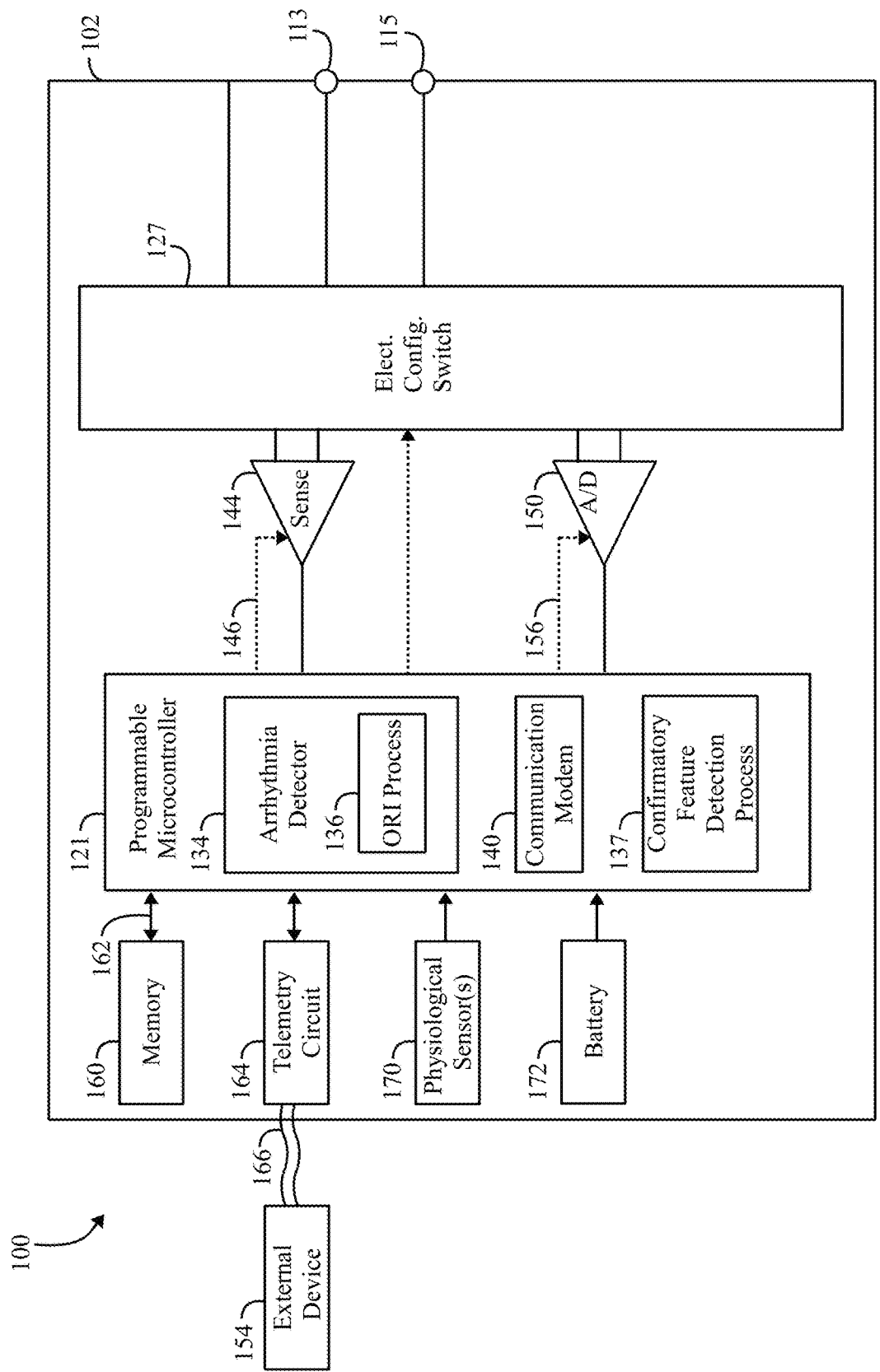
FIG. 16A shows a block diagram of the ICM formed in accordance with embodiments herein.

FIG. 16A shows a block diagram of the ICM 100 formed in accordance with embodiments herein. The ICM 100 may be implemented to monitor ventricular activity alone, or both ventricular and atrial activity through sensing circuit. The ICM 100 has a housing 102 to hold the electronic/computing components. The housing 102 (which is often referred to as the "can", "case", "encasing", or "case electrode") may be programmably selected to act as an electrode for certain sensing modes. Housing 102 further includes a connector (not shown) with at least one terminal 113 and optionally additional terminals 115. The terminals 113, 115 may be coupled to sensing electrodes that are provided upon or immediately adjacent the housing 102. Optionally, more than two terminals 113, 115 may be provided in order to support more than two sensing electrodes, such as for a bipolar sensing scheme that uses the housing 102 as a reference electrode. Additionally, or alternatively, the terminals 113, 115 may be connected to one or more leads having one or more electrodes provided thereon, where the electrodes are located in various locations about the heart. The type and location of each electrode may vary.

The ICM 100 includes a programmable microcontroller 121 that controls various operations of the ICM 100, including cardiac monitoring. Microcontroller 121 includes a microprocessor (or equivalent control circuitry), RAM and/or ROM memory, logic and timing circuitry, state machine circuitry, and I/O circuitry. The microcontroller 121 also performs the operations described herein in connection with collecting cardiac activity data and analyzing the cardiac activity data to identify AF episodes.

A switch 127 is optionally provided to allow selection of different electrode configurations under the control of the microcontroller 121. The electrode configuration switch 127 may include multiple switches for connecting the desired electrodes to the appropriate I/O circuits, thereby facilitating electrode programmability. The switch 127 is controlled by a control signal from the microcontroller 121. Optionally, the switch 127 may be omitted and the I/O circuits directly connected to the housing electrode 114 and a second electrode 126. Microcontroller 121 includes an arrhythmia detector 134 that is configured to analyze cardiac activity signals to identify potential AF episodes as well as other arrhythmias (e.g., Tachcardias, Bradycardias, Asystole, etc.). By way of example, the arrhythmia detector 134 may implement an AF detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and managing pacing therapies.

The ICM 100 is further equipped with a communication modem (modulator/demodulator) 140 to enable wireless communication. In one implementation, the communication modem 140 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 140 may be implemented in hardware as part of the microcontroller 121, or as software/firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 100 includes sensing circuit 144 selectively coupled to one or more electrodes that perform sensing operations, through the switch 127 to detect cardiac activity data indicative of cardiac activity. The sensing circuit 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 127 may be used to determine the sensing polarity of the cardiac signal by selectively closing the appropriate switches.

The output of the sensing circuit 144 is connected to the microcontroller 121 which, in turn, determines when to store the cardiac activity data of CA signals (digitized by the A/D data acquisition system 150) in the memory 160. For example, the microcontroller 121 may only store the cardiac activity data (from the A/D data acquisition system 150) in the memory 160 when a potential AF episode is detected. The sensing circuit 144 receives a control signal 146 from the microcontroller 121 for purposes of controlling the gain, threshold, polarization charge removal circuitry (not shown), and the timing of any blocking circuitry (not shown) coupled to the inputs of the sensing circuit.

In the example of FIG. 6, a single sensing circuit 144 is illustrated. Optionally, the ICM 100 may include multiple sensing circuits, similar to sensing circuit 144, where each sensing circuit is coupled to two or more electrodes and controlled by the microcontroller 121 to sense electrical activity detected at the corresponding two or more electrodes. The sensing circuit 144 may operate in a unipolar sensing configuration or in a bipolar sensing configuration. Optionally, the sensing circuit 144 may be removed entirely and the microcontroller 121 perform the operations described herein based upon the CA signals from the A/D data acquisition system 150 directly coupled to the electrodes.

The arrhythmia detector 134 of the microcontroller 121 includes an on-board R-R interval irregularity (ORI) process 136 that detects AF episodes using R-R interval irregularities as discussed in connection with FIGS. 17-18. The ORI process 136 may be implemented as firmware, software and/or circuits. The ORI process 136 uses a hidden Markov Chains and Euclidian distance calculations of similarity to assess the transitionary behavior of one R-wave (RR) interval to another and compare the patient's RR interval transitions to the known RR interval transitions during AF and non-AF episodes obtained from the same patient and/or many patients. The ORI process 136 detects AF episodes over a short number of RR intervals. For example, the ORI process 136 may implement the AF detection methods described in U.S. Pat. No. 8,135,456, the complete subject matter of which is incorporated herein by reference in its entirety.

As explained herein, the ORI process 136 utilizes the R-wave detection and/or noise detection processes 137 described herein in connection with FIGS. 2-15 to detect R-waves and to detect noise. The ORI process 136 applies a direction related responsiveness (DRR) filter to the CA signals to produce DRR filtered signals, and compares a current sample from the CA signals to a prior sample from the DRR filtered signals to identify a direction characteristic of the CA signals. The ORI process 136 defines a filter coefficient of the DRR filter based on a timing constant that is set based on the direction characteristic identified, analyzes the CA signals in connection with the DRR filtered signals to identify a peak characteristic of the CA signals, and determines peak to peak intervals between successive peak characteristics. The ORI process detects at least one of noise or an arrhythmia based on the peak to peak intervals, and records the results of the detecting.

Additionally, or alternatively, the ORI process 136 are further configured for setting the time constant to a first value when the direction characteristic indicates an increasing trend in the CA signals and setting the time constant to a second value when the direction characteristic indicates a decreasing trend in the CA signals. The first value represents a time constant that is shorter than the second value. Additionally, or alternatively, the ORI process 136 are further configured for determining a difference between the current sample of the CA signals and a prior sample of the DRR filtered signals and determining whether the difference exceeds a threshold. Additionally, or alternatively, the ORI process 136 are further configured for declaring detection of a peak of an R-wave when the difference exceeds the threshold. Additionally, or alternatively, the ORI process 136 are further configured for identifying the peak characteristic as a peak of an R-wave, the determining comprises determining the peak to peak intervals as RR intervals, and the detecting comprises detecting the arrhythmia based on the RR intervals. Additionally, or alternatively, the ORI process 136 are further configured for identifying the peak characteristic as a noise peak, the determining comprises declaring a noise peak to peak (NPP) interval when the peak to peak interval is below a threshold.

The ORI process 136 tracks RR intervals within the CA signal and identifies AF events within the CA signal based on irregularities in the RR interval. When a sufficient number (e.g., X cardiac events out of Y cardiac events) of the cardiac events within the CA signal are identified as AF events, the ORI process 136 declares an AF episode.

Returning to FIG. 2A, the ICM 100 further includes an analog-to-digital A/D data acquisition system (DAS) 150 coupled to one or more electrodes via the switch 127 to sample cardiac activity signals across any pair of desired electrodes. The data acquisition system 150 is configured to acquire cardiac electrogram (EGM) signals as CA signals, convert the raw analog data into digital data, and store the digital data as CA data for later processing and/or telemetric transmission to an external device 154 (e.g., a programmer, local transceiver, or a diagnostic system analyzer). The data acquisition system 150 is controlled by a control signal 156 from the microcontroller 121. The EGM signals may be utilized as the cardiac activity data that is analyzed for potential AF episodes. The ACS adjustment and ORI process 136 may be applied to signals from the sensing circuit 144 and/or the DAS 150.

By way of example, the external device 154 may represent a bedside monitor installed in a patient's home and utilized to communicate with the ICM 100 while the patient is at home, in bed or asleep. The external device 154 may be a programmer used in the clinic to interrogate the ICM 100, retrieve data and program detection criteria and other features. The external device 154 may be a handheld device (e.g., smartphone, tablet device, laptop computer, smartwatch and the like) that can be coupled over a network (e.g., the Internet) to a remote monitoring service, medical network and the like. The external device 154 facilitates access by physicians to patient data as well as permitting the physician to review real-time CA signals while collected by the ICM 100.

The microcontroller 121 is coupled to a memory 160 by a suitable data/address bus 162. The programmable operating parameters used by the microcontroller 121 are stored in memory 160 and used to customize the operation of the ICM 100 to suit the needs of a particular patient. Such operating parameters define, for example, detection rate thresholds, sensitivity, automatic features, AF detection criteria, activity sensing or other physiological sensors, and electrode polarity, etc.

In addition, the memory 160 stores the cardiac activity data, as well as the markers and other data content associated with detection of arrhythmia episodes. The operating parameters of the ICM 100 may be non-invasively programmed into the memory 160 through a telemetry circuit 164 in telemetric communication via communication link 166 with the external device 154. The telemetry circuit 164 allows intracardiac electrograms and status information relating to the operation of the ICM 100 (as contained in the microcontroller 121 or memory 160) to be sent to the external device 154 through the established communication link 166. In accordance with embodiments herein, the telemetry circuit 164 conveys the cardiac activity data, markers and other information related to AF episodes.

The ICM 100 may further include magnet detection circuitry (not shown), coupled to the microcontroller 121, to detect when a magnet is placed over the unit. A magnet may be used by a clinician to perform various test functions of the housing 102 and/or to signal the microcontroller 121 that the external device 154 is in place to receive or transmit data to the microcontroller 121 through the telemetry circuits 164.

The ICM 100 can further include one or more physiologic sensors 170. Such sensors are commonly referred to (in the pacemaker arts) as "rate-responsive" or "exercise" sensors. The physiological sensor 170 may further be used to detect changes in the physiological condition of the heart, or diurnal changes in activity (e.g., detecting sleep and wake states). Signals generated by the physiological sensors 170 are passed to the microcontroller 121 for analysis and optional storage in the memory 160 in connection with the cardiac activity data, markers, episode information and the like. While shown as being included within the housing 102, the physiologic sensor(s) 170 may be external to the housing 102, yet still be implanted within or carried by the patient. Examples of physiologic sensors might include sensors that, for example, activity, temperature, sense respiration rate, pH of blood, ventricular gradient, activity, heart sounds, position/posture, minute ventilation (MV), and so forth.

A battery 172 provides operating power to all of the components in the ICM 100. The battery 172 is capable of operating at low current drains for long periods of time. The battery 172 also desirably has a predictable discharge characteristic so that elective replacement time can be detected. As one example, the housing 102 employs lithium/silver vanadium oxide batteries. The battery 172 may afford various periods of longevity (e.g., three years or more of device monitoring). In alternate embodiments, the battery 172 could be rechargeable. See for example, U.S. Pat. No. 7,294,108, Cardiac event micro-recorder and method for implanting same, which is hereby incorporated by reference.

The ICM 100 provides a simple to configure data storage option to enable physicians to prioritize data based on individual patient conditions, to capture significant events and reduce risk that unexpected events are missed. The ICM 100 may be programmable for pre- and post-trigger event storage. For example, the ICM 100 may be automatically activated to store 10-120 seconds of CA data prior to an event of interest and/or to store 10-120 seconds of post CA data. Optionally, the ICM 100 may afford patient triggered activation in which pre-event CA data is stored, as well as post event CA data (e.g., pre-event storage of 1-15 minutes and post-event storage of 1-15 minutes). Optionally, the ICM 100 may afford manual (patient triggered) or automatic activation for CA data. Optionally, the ICM 100 may afford additional programming options (e.g., asystole duration, bradycardia rate, tachycardia rate, tachycardia cycle count). The amount of CA data storage may vary based upon the size of the memory 160.

The ICM 100 may provide comprehensive safe diagnostic data reports including a summary of heart rate, in order to assist physicians in diagnosis and treatment of patient conditions. By way of example, reports may include episodal diagnostics for auto trigger events, episode duration, episode count, episode date/time stamp and heart rate histograms. The ICM 100 may be configured to be relatively small (e.g., between 2-10 cc in volume) which may, among other things, reduce risk of infection during implant procedure, afford the use of a small incision, afford the use of a smaller subcutaneous pocket and the like. The small footprint may also reduce implant time and introduce less change in body image for patients.

Figure 16B:
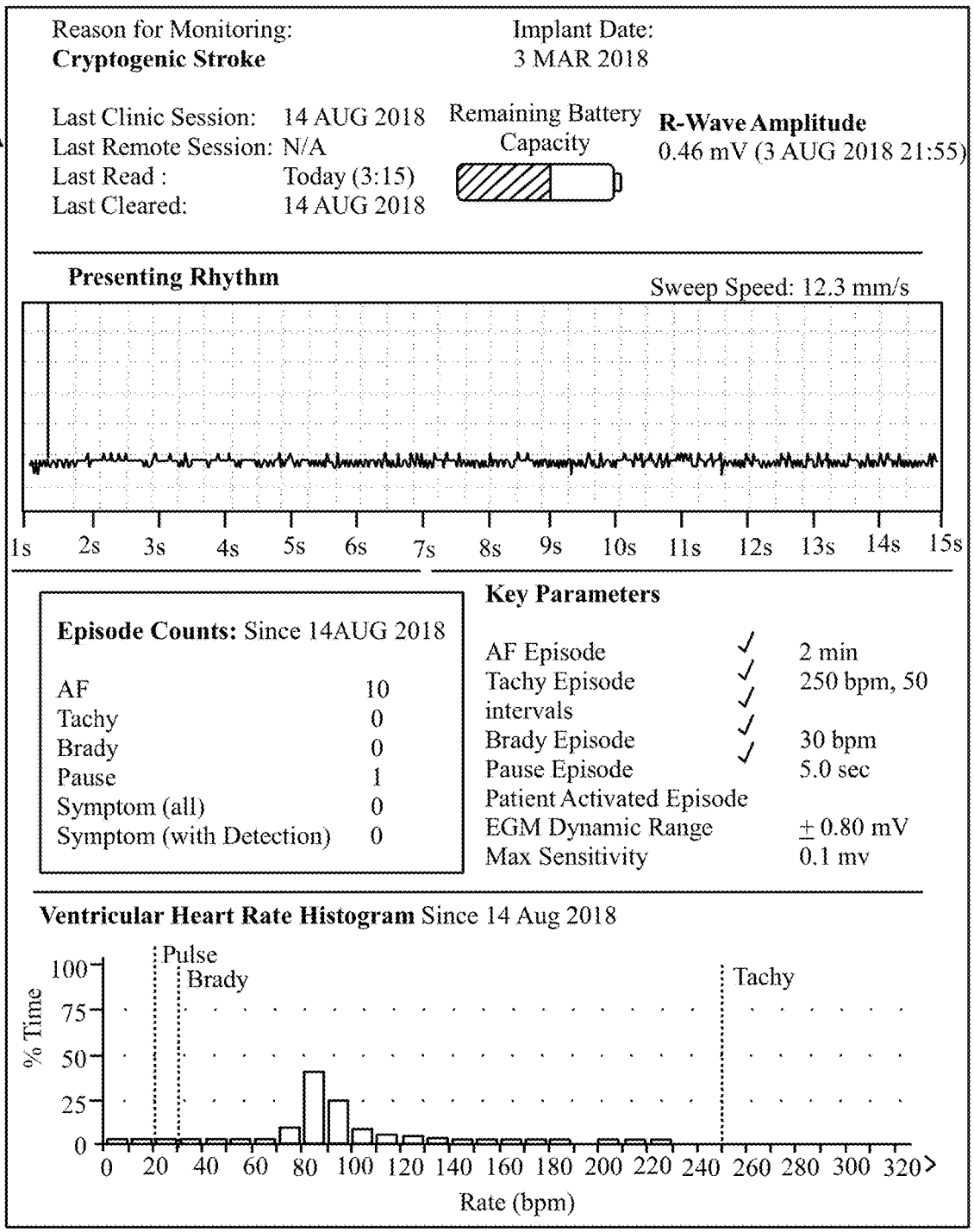
FIG. 16B illustrates screenshots of displays in which episode statistics and arrhythmia diagnostics may be presented to a physician in accordance with an embodiment herein.
Figure 16C:
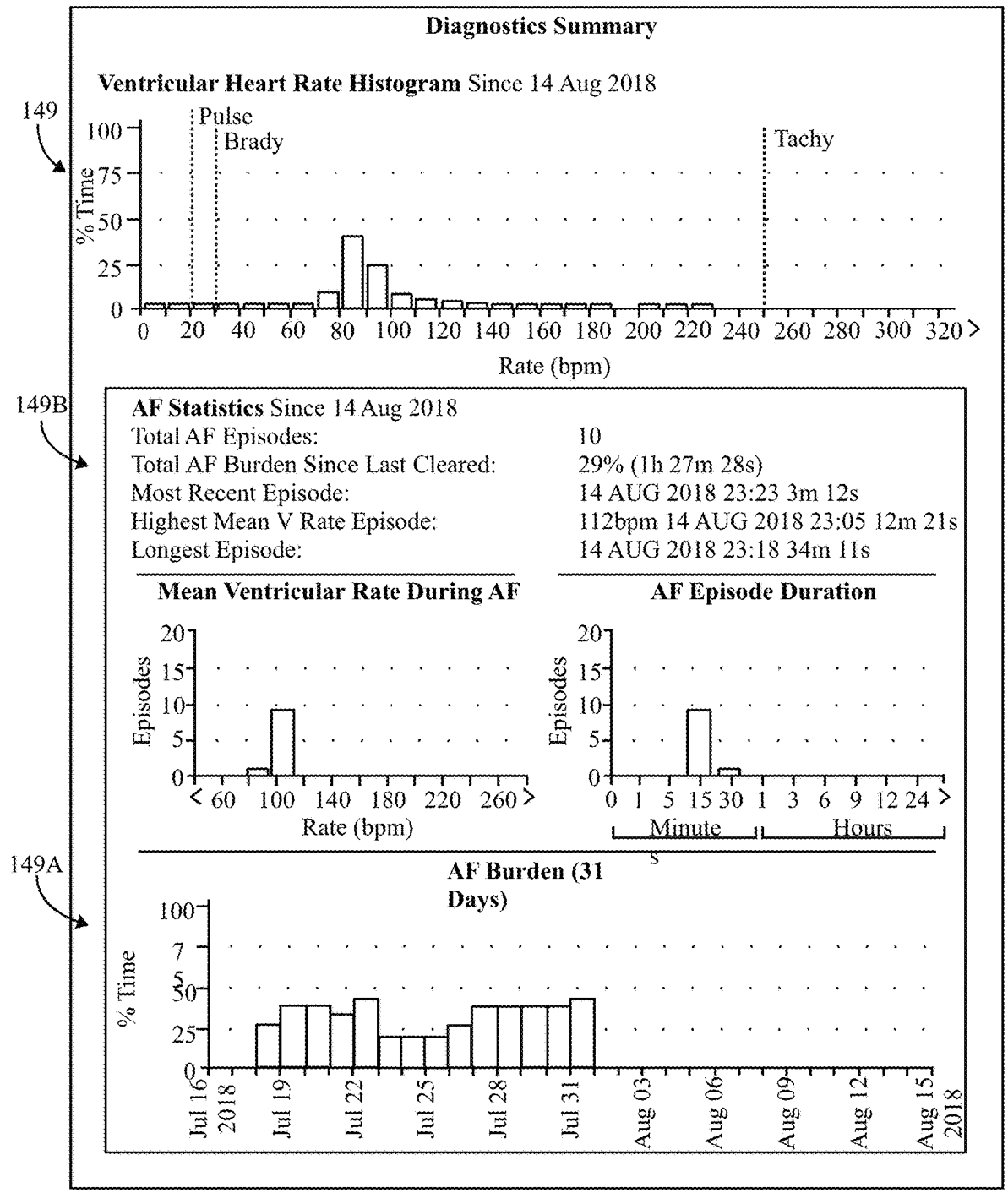
FIG. 16C illustrates screenshots of displays in which episode statistics and arrhythmia diagnostics may be presented to a physician in accordance with embodiments herein.

FIGS. 16B and 16C illustrate screenshots of displays in which episode statistics 147 and arrhythmia diagnostics may be presented to a physician in accordance with an embodiment herein. The arrhythmia diagnostics 149 may represent cumulative diagnostic information for a period of time, such as when the diagnostics data is last cleared from the ICM. The arrhythmia diagnostics 149 may include various information concerning heart rate, such as ventricular heart rate histograms, dates and times of last programmer sessions, diagnostic data last read, diagnostic data last cleared and the like. The arrhythmia diagnostics 149 may also include AF diagnostics, such as AF burden 149A, AF summaries, AF statistical data 149B, dates and times of last programmer session, last time the AF diagnostic data were read, last time the AF diagnostic data was cleared and the like. By way of example, AF burden may be displayed in an AF diagnostics window of a computing device formatted as one or more bar graphs of a percentage of time that the patient experienced AF during a predetermined period of time (e.g., each day, each week, each month). The AF burden may show a percentage of time that the patient was in AF since the AF diagnostics data were last cleared. The AF summary may include one or more graphs of mean ventricular heart rate and a duration of AF episodes since the AF diagnostic data were last cleared. The AF diagnostic data may accrue various cumulative totals concerning AF episodes detected and/or stored since the AF diagnostic data were last cleared. The AF statistics may include, among other things, a total number of AF episodes, AF burden trends, AF episode duration histograms, mean ventricular rate during AF and the like.

Optionally, an enhanced confirmatory AF detection process is implemented to analyze the results of the baseline analysis performed by the ORI process in the ICM. The enhanced confirmatory AF detection process determines whether AF episodes declared by the ICM are true or false, and updates the AF diagnostics in connection there with. Next, various processes are described in connection with embodiments herein that are performed by one or more of the circuits, processors and other structures illustrated in the Figures and described in the specification.

Figure 17:
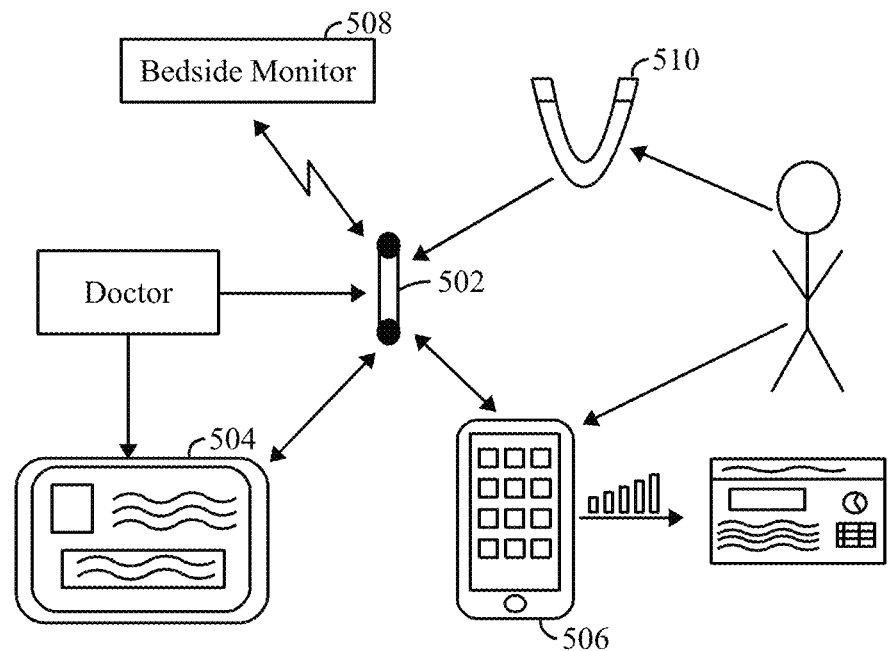
FIG. 17 illustrates a system level diagram indicating devices and networks that may utilize the methods and systems herein in accordance with embodiments herein.

FIG. 17 illustrates a system level diagram indicating devices and networks that may utilize the methods and systems herein. For example, an implantable cardiac monitoring device (ICM) 502 may be utilized to collect a cardiac activity data set. The ICM 502 may supply the CA data set (CA signals and DD feature markers) to various local external devices, such as a tablet device 504, a smart phone 506, a bedside monitoring device 508, a smart watch and the like. The devices 504-508 include a display to present the various types of CA signals, markers, statistics, diagnostics and other information described herein. The ICM 502 may convey the CA data set over various types of wireless communications links to the devices 504, 506 and 508. The ICM 502 may utilize various communications protocols and be activated in various manners, such as through a Bluetooth, Bluetooth low energy, WiFi or other wireless protocol. Additionally, or alternatively, when a magnetic device 510 is held next to the patient, the magnetic field from the device 510 may activate the ICM 502 to transmit the cardiac activity data set and AF data to one or more of the devices 504-508.

The processes described herein for analyzing the cardiac activity signals to identify R-waves and/or noise and to identify AF, may be implemented on one or more of the devices 504-508. Additionally, or alternatively, the ICM 502 may also implement the processes described herein. The devices 504-508 may present the CA data set and AF detection statistics and diagnostics to clinicians in various manners. As one example, AF markers may be illustrated on EGM signal traces. AF and sinus markers may be presented in a marker channel that is temporally aligned with original or modified CA signals. Additionally, or alternatively, the duration and heart rate under AF may be formatted into histograms or other types of charts to be presented alone or in combination with CA signals.

Figure 18:
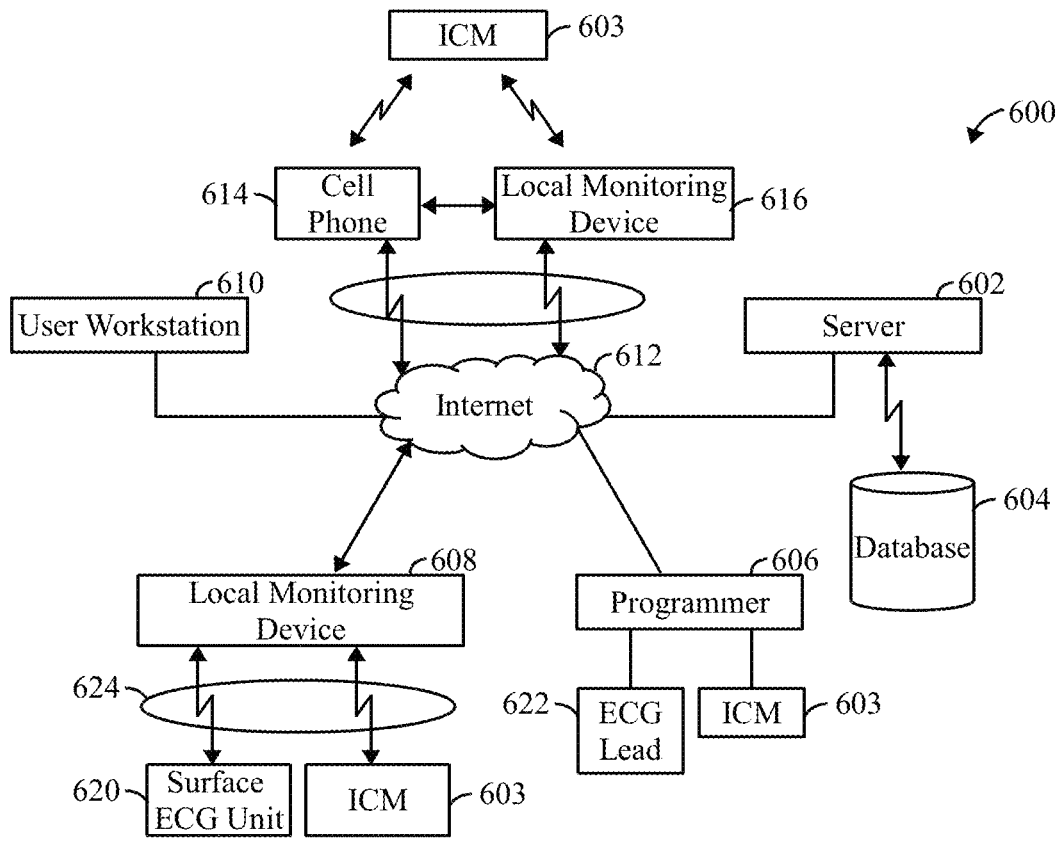
FIG. 18 illustrates a distributed processing system in accordance with embodiments herein.

FIG. 18 illustrates a distributed processing system 600 in accordance with embodiments herein. The distributed processing system 600 includes a server 602 connected to a database 604, a programmer 606, a local monitoring device 608 and a user workstation 610 electrically connected to a network 612. Any of the processor-based components in FIG. 6 (e.g., workstation 610, cell phone 614, local monitoring device 616, server 602, programmer 606) may perform the processes discussed herein.

The network 612 may provide cloud-based services over the internet, a voice over IP (VoIP) gateway, a local plain old telephone service (POTS), a public switched telephone network (PSTN), a cellular phone based network, and the like. Alternatively, the communication system may be a local area network (LAN), a medical campus area network (CAN), a metropolitan area network (MAN), or a wide area network (WAM). The communication system serves to provide a network that facilitates the transfer/receipt of data and other information between local and remote devices (relative to a patient). The server 602 is a computer system that provides services to the other computing devices on the network 612. The server 602 controls the communication of information such as cardiac activity data sets, bradycardia episode information, asystole episode information, AF episode information, markers, cardiac signal waveforms, heart rates, and device settings. The server 602 interfaces with the network 612 to transfer information between the programmer 606, local monitoring devices 608, 616, user workstation 610, cell phone 614 and database 604. The database 604 stores information such as cardiac activity data, AF episode information, AF statistics, diagnostics, markers, cardiac signal waveforms, heart rates, device settings, and the like, for a patient population. The information is downloaded into the database 604 via the server 602 or, alternatively, the information is uploaded to the server 602 from the database 604. The programmer 606 may reside in a patient's home, a hospital, or a physician's office. The programmer 606 may wirelessly communicate with the ICM 603 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 606 to the ICM 603. The programmer 606 is able to acquire ECG 622 from surface electrodes on a person (e.g., ECGs), electrograms (e.g., EGM) signals from the ICM 603, and/or cardiac activity data, AF episode information, AF statistics, diagnostics, markers, cardiac signal waveforms, atrial heart rates, device settings from the ICM 603. The programmer 606 interfaces with the network 612, either via the internet, to upload the information acquired from the surface ECG unit 620, or the ICM 603 to the server 602.

The local monitoring device 608 interfaces with the communication system to upload to the server 602 one or more of cardiac activity data set, AF episode information, AF statistics, diagnostics, markers, cardiac signal waveforms, heart rates, sensitivity profile parameter settings and detection thresholds. In one embodiment, the surface ECG unit 620 and the ICM 603 have a bi-directional connection 624 with the local RF monitoring device 608 via a wireless connection. The local monitoring device 608 is able to acquire cardiac signals from the surface of a person, cardiac activity data sets and other information from the ICM 603, and/or cardiac signal waveforms, heart rates, and device settings from the ICM 603. On the other hand, the local monitoring device 608 may download the data and information discussed herein from the database 604 to the surface ECG unit 620 or the ICM 603.

The user workstation 610 may be utilized by a physician or medical personnel to interface with the network 612 to download cardiac activity data and other information discussed herein from the database 604, from the local monitoring devices 608, 616, from the ICM 603 or otherwise. Once downloaded, the user workstation 610 may process the CA data in accordance with one or more of the operations described above. The user workstation 610 may upload/push settings (e.g., sensitivity profile parameter settings), ICM instructions, other information and notifications to the cell phone 614, local monitoring devices 608, 616, programmer 606, server 602 and/or ICM 603. For example, the user workstation 610 may provide instructions to the ICM 603 in order to update sensitivity profile parameter settings when the ICM 603 declares too many false AF detections.

The processes described herein in connection with analyzing cardiac activity data for detecting R-waves/noise and for confirming, or rejecting, AF detection may be performed by one or more of the devices illustrated in FIG. 6, including but not limited to the ICM 603, programmer 606, local monitoring devices 608, 616, user workstation 610, cell phone 614, and server 602. The process described herein may be distributed between the devices of FIG. 6.

Closing

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an Infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise Indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are Intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A computer implemented method for detecting arrhythmias in cardiac activity, comprising:
   under control of one or more processors configured with specific executable instructions,
   obtaining far field cardiac activity (CA) signals;
   applying a direction related responsiveness (DRR) filter to the CA signals to produce DRR filtered signals;
   comparing a current sample from the CA signals to a prior sample from the DRR filtered signals to identify a direction characteristic of the CA signals;
   defining the DRR filter based on a timing constant that is set based on the direction characteristic identified;
   analyzing the CA signals in connection with the DRR filtered signals to identify a peak characteristic of the CA signals;
   determining peak to peak intervals between successive peak characteristics; and
   detecting at least one of noise or an arrhythmia based on the peak to peak intervals; and
   recording results of the detecting.

2. The method of claim 1, further comprising setting the time constant to a first value when the direction characteristic indicates an increasing trend in the CA signals and setting the time constant to a second value when the direction characteristic indicates a decreasing trend in the CA signals.

3. The method of claim 2, wherein the first value represents a time constant that is shorter than the second value.

4. The method of claim 2, wherein the first value is used by the DRR filter to produce the DRR filtered signals that respond to the decreasing trend in the CA signals more slowly as compared to a responsiveness of the DRR filter when set to the second value in response to the increasing trend in the CA signals.

5. The method of claim 1, wherein the analyzing operation comprises determining a difference between the current sample of the CA signals and a prior sample of the DRR filtered signals and determines whether the difference exceeds a threshold.

6. The method of claim 5, further comprising declaring detection of a peak of an R-wave when the difference exceeds the threshold.

7. The method of claim 1, wherein the analyzing comprises identifying the peak characteristic as a peak of an R-wave, the determining comprises determining the peak to peak intervals as RR intervals, and the detecting comprises detecting the arrhythmia based on the RR intervals.

8. The method of claim 1, wherein the analyzing comprises identifying the peak characteristic as a noise peak, the determining comprises declaring a noise peak to peak (NPP) interval when the peak to peak interval is below a threshold.

9. The method of claim 8, further comprising declaring a segment of the CA signals to include excessive noise when a select number of the peak to peak intervals are declared to be NPP intervals.

10. The method of claim 9, further comprising removing the segment of the CA signals to form noise corrected CA signals, and repeating the applying, comparing, defining, analyzing, determining and detecting operations utilizing a DRR filter and time constant set for R-wave detection.

11. A system for detecting arrhythmias in cardiac activity, comprising:
 memory to store specific executable instructions;
 one or more processors configured to execute the specific executable instructions for:
  obtaining far field cardiac activity (CA) signals for beats;
  applying a direction related responsiveness (DRR) filter to the CA signals to produce DRR filtered signals;
  comparing a current sample from the CA signals to a prior sample from the DRR filtered signals to identify a direction characteristic of the CA signals;
  defining the DRR filter based on a timing constant that is set based on the direction characteristic identified;
  analyzing the CA signals in connection with the DRR filtered signals to identify a peak characteristic of the CA signals;
  determining peak to peak intervals between successive peak characteristics; and
  detecting at least one of noise or an arrhythmia based on the peak to peak intervals; and
  recording results of the detecting.

12. The system of claim 11, wherein the one or more processors are further configured for setting the time constant to a first value when the direction characteristic indicates an increasing trend in the CA signals and setting the time constant to a second value when the direction characteristic indicates a decreasing trend in the CA signals.

13. The system of claim 12, wherein the first value represents a time constant that is shorter than the second value.

14. The system of claim 11, wherein the one or more processors are further configured for determining a difference between the current sample of the CA signals and a prior sample of the DRR filtered signals and determining whether the difference exceeds a threshold.

15. The system of claim 11, wherein the one or more processors are further configured for declaring detection of a peak of an R-wave when the difference exceeds the threshold.

16. The system of claim 11, wherein the one or more processors are further configured for identifying the peak characteristic as a peak of an R-wave, the determining comprises determining the peak to peak intervals as RR Intervals, and the detecting comprises detecting the arrhythmia based on the RR intervals.

17. The system of claim 11, wherein the analyzing comprises identifying the peak characteristic as a noise peak, the determining comprises declaring a noise peak to peak (NPP) interval when the peak to peak interval is below a threshold.

18. The system of claim 11, further comprising an implantable medical device housing the processor and memory.

19. The system of claim 11, wherein the processor and memory are housed within at least one of a local external device and a remote server.

20. The system of claim 11, wherein the one or more processors are configured to perform the repeating the applying, comparing, defining, analyzing, determining and detecting operations in connection with at least one of i) an arrhythmia first pass detection process or ii) an arrhythmia second pass confirmation process.

* * * * *